(12) United States Patent
Collins et al.

(10) Patent No.: US 8,153,119 B2
(45) Date of Patent: Apr. 10, 2012

(54) ENGINEERED ENZYMATICALLY ACTIVE BACTERIOPHAGE AND METHODS FOR DISPERSING BIOFILMS

(75) Inventors: James J Collins, Newton Center, MA (US); Timothy Kuan-Ta Lu, Boston, MA (US)

(73) Assignees: Trustees of Boston University, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/337,677

(22) Filed: Dec. 18, 2008

(65) Prior Publication Data
US 2009/0155215 A1  Jun. 18, 2009

Related U.S. Application Data

(60) Provisional application No. 61/014,518, filed on Dec. 18, 2007.

(51) Int. Cl.
*A01N 63/00* (2006.01)
*A61K 38/43* (2006.01)
*C12P 21/06* (2006.01)
*C12P 21/04* (2006.01)
*C12N 15/09* (2006.01)
*C12N 15/00* (2006.01)
*C12N 1/00* (2006.01)

(52) U.S. Cl. ............... 424/93.6; 424/93.1; 424/94.1; 435/69.1; 435/69.2; 435/71.1; 435/320.1; 435/243

(58) Field of Classification Search .................. None
See application file for complete search history.

(56) References Cited

U.S. PATENT DOCUMENTS

| | | |
|---|---|---|
| 2002/0037260 A1 | 3/2002 | Budny et al. |
| 2006/0140911 A1* | 6/2006 | Sharp et al. ............ 424/93.6 |
| 2011/0008402 A1 | 1/2011 | Madhyastha et al. |

FOREIGN PATENT DOCUMENTS

WO 2006137847 12/2006

OTHER PUBLICATIONS

Kaplan et al. J. Bact. 186:8213-8220; 2001.*
Slootweg et al. NAR 00:e1-11; 2006.*
Beck et al. J. Bact. 173:947-954; 1991.*
Lu et al, Dispersing biofilms with engineered enzymatic bacteriophage. Proc Natl Acad Sci U S A. 104(27):11197-202, 2007.*
Shuren, J (2006), ed. U.S. Food and Drug Administration, H (Federal Register, vol. 71, pp. 47729-47732.
Studier, F.W. and Dunn, J. J., "Organization and Expression of Bacteriophage T7 DNA." Cold Spring Harb Symp Quant Biol. 47(Pt 2):999-1007, 1983.
Studier, F. W., "Bacteriophage T7." Science 176:367-376, 1972.
Anderson, JC et al., "Environmentally Controlled Invasion of Cancer Cells by Engineered Bacteria." J. Mol. Biol. 355:619-627, 2006.
Andrianantoandro, E et al., "Synthetic biology: new engineering rules for an emerging discipline." Molecular Systems Biology 2:2006.0028:1-14, 2006.
Aslam, S et al., "Treatment of Clostridium difficile-associated disease: old therapies and new strategies." Lancet Infect Dis 5:549-557, 2005.
Boratyński, J et al., "Preparation of Endotoxin-free Bacteriophages." Cellular and Molecular Biology Letters 9:253-259, 2004.
Ceri, H et al., "The Calgary Biofilm Device: New Technology for Rapid Determination of Antibiotic Susceptibilities of Bacterial Biofilms." Journal of Clinical Microbiology 37(6):1771-1776, 1999.
Chan, Ly et al., "Refactoring bacteriophage T7." Molecular Systems Biology 1:2005.0018:1-10, 2005.
Costerton, JW et al., "Bacterial Biofilms: A Common Cause of Persistent Infections." Science 284:1318-1322, 1999.
Curtin, JJ et al., "Using Bacteriophages To Reduce Formation of Catheter-Associated Biofilms by Staphylococcus epidermidis." Antimicrobial Agents and Chemotherapy 50(4):1268-1275, 2006.
Datsenko, KA and BL Wanner, "One-step inactivation of chromosomal genes in *Escherichia coli* K-12 using PCR products." PNAS 97(12):6640-6645, 2000.
Davey, ME and GA O'Toole, "Microbial Biofilms: from Ecology to Molecular Genetics." Microbiology and Molecular Biology Reviews 64(4):847-867, 2000.
Doulatov, S et al., "Tropism switching in Bordetella bacteriophage defines a family of diversity-generating retroelements." Nature 431:476-481, 2004.
Endy, D, "Foundations for engineering biology." Nature 438:449-453, 2005.
García, LR and IJ Molineux, "Incomplete Entry of Bacteriophage T7 DNA into F Plasmid-Containing *Escherichia coli*." Journal of Bacteriology 177(14):4077-4083, 1995.
Ghigo, J-M, "Natural conjugative plasmids induce bacterial biofilm development." Nature 412:442-445, 2001.
Hagens, S et al., "Therapy of Experimental Pseudomonas Infections with a Nonreplicating Genetically Modified Phage." Antimicrobial Agents and Chemotherapy 48(10):3817-3822, 2004.
Hagens, S and U Bläsi, "Genetically modified filamentous phage as bactericidal agents: a pilot study." Letters in Applied Microbiology 37:318-323, 2003.
Hasty, J et al., "Engineered gene circuits." Nature 420:224-230, 2002.
Hickman-Brenner, FW et al., "Phage Typing of Salmonella enteritidis in the United States." Journal of Clinical Microbiology 29(12):2817-2823, 1991.
Hughes, KA et al., "Bacteriophage and associated polysaccharide depolymerases—novel tools for study of bacterial biofilms." Journal of Applied Microbiology 85:583-590, 1998.

(Continued)

*Primary Examiner* — Sumesh Kaushal
(74) *Attorney, Agent, or Firm* — Nixon Peabody LLP; Ronald I. Eisenstein; Leena H. Karttunen Contarino

(57) ABSTRACT

The present invention is directed to engineered enzymatically active bacteriophages that are both capable of killing the bacteria by lysis and dispersing the bacterial biofilm because they have been also engineered to express biofilm-degrading enzymes, particularly dispersin B (DspB), an enzyme that hydrolyzes β-1,6-N-acetyl-D-glucosamine, a crucial adhesion molecule needed for biofilm formation and integrity in *Staphylococcus* and *E. coli*, including *E. coli* K-12, as well as clinical isolates.

10 Claims, 13 Drawing Sheets

OTHER PUBLICATIONS

Itaya, M et al., "Combining two genomes in one cell: Stable cloning of the Synechocystis PCC6803 genome in the Bacillus subtilis 168 genome." PNAS 102(44):15971-15976, 2005.

Itoh, Y et al., "Depolymerization of β-1,6-N-Acetyl-D-Glucosamine Disrupts the Integrity of Diverse Bacterial Biofilms." Journal of Bacteriology 187(1):382-387, 2005.

Hoffman, LR et al., "Aminoglycoside antibiotics induce bacterial biofilm formation." Nature 436:1171-1175, 2005.

Hughes, KA et al., "Biofilm susceptibility to bacteriophage attack: the role of phage-borne polysaccharide depolymerase." Microbiology 144:3039-3047, 1998.

Jackson, DW et al., "Biofilm Formation and Dispersal under the Influence of the Global Regulator CsrA of *Escherichia coli*." Journal of Bacteriology 184(1):290-301, 2002.

Kolter, R and EP Greenberg, "The superficial life of microbes." Nature 441:300-302, 2006.

Liu, M et al., "Reverse Transcriptase-Mediated Tropism Switching in Bordatella Bacteriophage." Science 295:2091-2094, 2002.

Loose, C et al., "A linguistic model for the rational design of antimicrobial peptides." Nature 443:867-869, 2006.

Merril, CR et al., "The prospect for bacteriophage therapy in Western medicine." Nature Reviews 2:489-497, 2003.

Merril, CR et al., "Long-circulating bacteriophage as antibacterial agents." Proc. Natl. Acad. Sci. USA 93:3188-3192, 1996.

Parsek, MR and PK Singh, "Bacterial Biofilms: An Emerging Link to Disease Pathogenesis." Annu. Rev. Microbiol. 57:677-701, 2003.

Projan, S, "Phage-inspired antibiotics?" Nature Biotechnology 22(2):167-168, 2004.

Re, SD et al., "Tight Modulation of *Escherichia coli* Bacterial Biofilm Formation through Controlled Expression of Adhesion Factors." Applied and Environmental Microbiology 73(10):3391-3403, 2007.

Ro, D-K et al., "Production of the antimalarial drug precursor artemisinic acid in engineered yeast." Nature 440:940-943, 2006.

Scholl, D et al., "*Escherichia coli* K1's Capsule Is a Barrier to Bacteriophage T7." Applied and Environmental Microbiology 71(8):4872-4874, 2005.

Schoolnik, GK et al., "Phage offer a real alternative." Nature Biotechnology 22(5):505-507, 2004.

Stewart, PS and JW Costerton, "Antiobiotic resistance of bacteria in biofilms." The Lancet 358:135-138, 2001.

Summers, WC, "Bacteriophage Therapy." Annu. Rev. Microbiol. 55:437-451, 2001.

Tian, J et al., "Accurate multiplex gene synthesis from programmable DNA microchips." Nature 432:1050-1054, 2004.

Wentworth, BB, "Bacteriophage Typing of the Staphylococci." Bacteriol Rev 27: 253-272, 1963.

Whitchurch, CB et al., "Extracellular DNA Required for Bacterial Biofilm Formation." Science 295:1487, 2002.

Xavier, JB et al., "Biofilm-control strategies based on enzymic disruption of the extracellular polymeric substance matrix—a modelling study." Microbiology 151:3817-3832, 2005.

Baker, D. et al., "Engineering Life: Building a FAB for Biology." Sci Am. 294(6):44-51, 2006.

Bartlett, J. G., MD, "Narrative Review: The New Epidemic of Clostridium difficile- Associated Enteric Disease." Ann. Intern. Med. 145:758-764, 2006.

Corbin, B. D. et al., "Bacteriophage T4 multiplication in a glucose-limited *Escherichia coli* biofilm." Can. J. Microbiol. 47:680-684, 2001.

Costerton, J. W. and Lewandowski, Z., "Microbial Biofilms." Annu. Rev. Microbiol. 49:711-745, 1995.

Doolittle, M.M. et al., "Tracing the interaction of bacteriophage with bacterial biofilms using fluorescent and chromogenic probes." Journal of Industrial Microbiology 16:331-341, 1996.

Doolittle, M. M. et al., "Lytic infection of *Escherichia coli* biofilms by bacteriophage T4." Can. J. Microbiol. 41:12-18, 1995.

Dunn, J. J. and Studier, F. W., "Complete Nucleotide Sequence of Bacteriophage T7 DNA and the Locations of T7 Genetic Elements." J. Mol. Biol. 166:477-535, 1983.

Krylov (Russian Journal of Genetics. 2001: 37(7): pp. 715-730).

Rosenberg et al. (inNovations. Dec. 1996; 6: pp. 2-14).

Office Action Issued on Aug. 15, 2011 in U.S. Appl. No. 11/662,551.

U.S. Appl. No. 11/662,551, filed Sep. 12, 2005.

* cited by examiner

ENGINEERED ENZYMATICALLY ACTIVE BACTERIOPHAGE AND METHODS FOR DISPERSING BIOFILMS

CROSS-REFERENCE TO RELATED APPLICATIONS

This application claims benefit of the a U.S. provisional patent application No. 61/014,518 filed Dec. 18, 2008, the content of which is incorporated herein by its entirety.

GOVERNMENT SUPPORT

This invention was made with Government Support under Contract No. EF-0425719 awarded by the National Science Foundation. The Government has certain rights in the invention.

BACKGROUND OF THE INVENTION

Bacterial biofilms are sources of contamination that are difficult to eliminate in a variety of industrial, environmental and clinical settings.

Biofilms are polymer structures secreted by bacteria to protect bacteria from various environmental attacks, and thus result also in protection of the bacteria from disinfectants and antibiotics. Biofilms may be found on any environmental surface where sufficient moisture and nutrients are present. Bacterial biofilms are associated with many human and animal health and environmental problems. For instance, bacteria form biofilms on implanted medical devices, e.g., catheters, heart valves, joint replacements, and damaged tissue, such as the lungs of cystic fibrosis patients. Biofilms also contaminate surfaces such as water pipes and the like, and render also other industrial surfaces hard to disinfect.

For example, catheters, in particular central venous catheters (CVCs), are one of the most frequently used tools for the treatment of patients with chronic or critical illnesses and are inserted in more than 20 million hospital patients in the USA each year. Their use is often severely compromised as a result of bacterial biofilm infection which is associated with significant mortality and increased costs. Catheters are associated with infection by many biofilm forming organisms such as *Staphylococcus epidermidis, Staphylococcus aureus, Pseudomonas aeruginosa, Enterococcus faecalis* and *Candida albicans* which frequently results in generalized blood stream infection. Approximately 250,000 cases of CVC-associated bloodstream infections occur in the US each year with an associated mortality of 12%-25% and an estimated cost of treatment per episode of approximately $25,000. Treatment of CVC-associated infections with conventional antimicrobial agents alone is frequently unsuccessful due to the extremely high tolerance of biofilms to these agents. Once CVCs become infected the most effective treatment still involves removal of the catheter, where possible, and the treatment of any surrounding tissue or systemic infection using antimicrobial agents. This is a costly and risky procedure and re-infection can quickly occur upon replacement of the catheter.

Bacteria in biofilms are highly resistant to antibiotics and host defenses and consequently are persistent sources of infection.

Antibiotic resistance in biofilms poses a significant hurdle to eliminating biofilms with conventional antimicrobial drugs, new anti-biofilm strategies should be explored.

Accordingly, there is a need for improved phages to degrade biofilm

SUMMARY OF THE INVENTION

The present invention is directed to engineered enzymatically active bacteriophages that are both capable of killing the bacteria by lysis and dispersing the bacterial biofilm because they have been also engineered to express biofilm-degrading enzymes, particularly dispersin B (DspB), an enzyme that hydrolyzes $\beta$-1,6-N-acetyl-D-glucosamine, a crucial adhesion molecule needed for biofilm formation and integrity in *Staphylococcus* and *E. coli*, including *E. coli* K-12, as well as clinical isolates (Itoh, Y, Wang, X, Hinnebusch, B J, Preston, J F & Romeo, T (2005) J Bacteriol 187: 382-387).

The invention is further directed to the uses of such engineered enzymatically active bacteriophages for removing bacterial biofilms and killing bacteria within such biofilms. In particular, the invention is directed for destroying biofilms associated with *Staphylococcus* and *E. coli*, including *E. coli* K-12, as well as clinical isolates as described in Itoh, et al., (Id.).

Bacteriophages (often known simply as "phages") are viruses that grow within bacteria. The name translates as "eaters of bacteria" and reflects the fact that as they grow, the majority of bacteriophages kill the bacterial host in order to release the next generation of bacteriophages. Naturally occurring bacteriophages are incapable of infecting anything other than specific strains of the target bacteria, underlying their potential for use as control agents.

Bacteriophages and their therapeutic uses have been the subject of much interest since they were first recognized early in the 20th century. Lytic bacteriophages are viruses that infect bacteria exclusively, replicate, disrupt bacterial metabolism and destroy the cell upon release of phage progeny in a process known as lysis. These bacteriophages have very effective antibacterial activity and in theory have several advantages over antibiotics. Most notably they replicate at the site of infection and are therefore available in abundance where they are most required; no serious or irreversible side effects of phage therapy have yet been described and selecting alternative phages against resistant bacteria is a relatively rapid process that can be carried out in days or weeks.

Bacteriophage have been used in the past for treatment of plant diseases, such as fireblight as described in U.S. Pat. No. 4,678,750. Also, Bacteriophages have been used to destroy biofilms (e.g., U.S. Pat. No. 6,699,701). In addition, systems using natural bacteriophages that encode biofilm destroying enzymes in general have been described. Art also provides a number of examples of lytic enzymes encoded by bacteriophages that have been used as enzyme dispersion to destroy bacteria (U.S. Pat. No. 6,335,012 and U.S. Patent Application Publication No. 2005/0004030). The Eastern European research and clinical trials, particularly in treating human diseases, such as intestinal infections, has apparently concentrated on use of naturally occurring phages and their combined uses (Lorch, A. (1999), "Bacteriophages: An alternative to antibiotics?" Biotechnology and Development Monitor, No. 39, p. 14-17).

For example, PCT Publication No. WO 2004/062677 provides a method of treating bacterial biofilm, wherein the method comprises use of a first bacteriophage that is capable of infecting a bacterium within said biofilm, and a first polysaccharide lyase enzyme that is capable of degrading a polysaccharide within said biofilm. However, other studies have showed that addition of alginate lyase to established *P. aeruginosa* biofilm caused no observable detachment of biofilm and thu use of lyases would not be optimal for biofilm treatment (Christensen et al., 2001).

WO/2006/137847 describes a bacteriophage that expresses a biofilm degarading enzyme attached to its surface.

We provide a novel modular design strategy in which phage that kill bacteria in a species-specific manner are engineered to express at least one of the most effective EPS-degrading enzymes specific to the target biofilm, particularly, for example, dispersin B.

This strategy permits the development of a diverse library of biofilm-dispersing phage rather than trying to isolate such phage from the environment. By multiplying within the biofilm and hijacking the bacterial machinery, engineered enzymatically-active phage achieves high local concentrations of both enzyme and lytic phage to target multiple biofilm components, even with small initial phage inoculations.

We have discovered that our invention provides rapid phage replication with subsequent bacterial lysis and expression of biofilm-degrading enzymes which renders this two-pronged attack strategy a surprisingly efficient, autocatalytic method for removing bacterial biofilms in environmental, industrial, and clinical settings. FIG. 1 shows a schematic representation of the invention.

As discussed in detail below, we have discovered that this approach is at least about two, or more, such as three or four orders of magnitude more efficient than use of a lytic phage alone. This is a significant improvement over any of the lytic phage therapies described before the present invention.

Also, a significant advantage compared to methods where enzymes are administered as dispersions or an added component to compositions containing lytic phages is that the use of the engineered enzymatically active bacteriophages of the present invention allows one to reduce or eliminate multiple applications of the composition during the treatment of a surface having a bacterial biofilm.

Moreover, unlike the controversial reports regarding use of lyase enzyme we have discovered that the phages expressing one or more biofilm degrading enzymes, for example dispersin B, are consistently effective for destroying mature biofilms.

Also, unlike the large quantities of phage required in the methods previously described, such as $10^8$ PFU of lytic phage by Hanlon et al., the present method is efficient using as little as about $10^2$ PFU of initial engineered phage without the need for reapplication of the phage composition due to its ability to multiply (Hanlon, G. W., Denyer, S. P., Olliff, C. J., and Ibrahim L. J., (2001). Reduction in exopolysaccharide viscosity as an aid to bacteriophage penetration through *Pseudomonas aeruginosa* biofilms. App. Env. Micro. 67, 2746-2753.).

Our design also removes the need to express, purify, and deliver large doses of enzyme to specific sites of infection that may be difficult to access, and should improve the efficacy of phage therapy at removing biofilms. Increasingly cost-effective genome sequencing and synthetic biology technologies, which include the refactoring of phage genomes and large-scale DNA synthesis, further enable the production of engineered enzymatic phage and significantly extend the repertoire of biofilm-degrading phage that have been isolated from the environment (Andrianantoandro, E, Basu, S, Karig, D K & Weiss, R (2006) Mol Syst Biol 2: 2006.0028; Chan, L Y, Kosuri, S & Endy, D (2005) Mol Syst Biol 1: 2005.0018; Itaya, M, Tsuge, K, Koizumi, M & Fujita, K (2005) Proc Natl Acad Sci USA 102: 15971-15976).

In one embodiment, and all the other embodiments of the invention, the invention provides an engineered enzymatically active T7 bacteriophage that expresses dispersin B enzyme (DspB) or a fragment thereof having the enzymatically active site of the dispersin B enzyme operably linked to a strong promoter, such as T7 φ10 promoter, wherein a nucleic acid sequence encoding a gene expanding or enhancing the infectivity and/or replication capacity of the T7 bacteriophage, such as T3 gene 1.2 is operably linked into a unique BclI site in the T7 phage and wherein a φ10-dspB construct is operably linked after the T7 phage capsid gene 10B.

In one embodiment the enzymatically active fragment of DspB has at least about 50% of the activity of the wild-type DspB, in one embodiment the activity is at least about 50-60% including all the integers in between, 60%, 70-100%, 70%, 80%, 90% or more or even more than 100% of the activity compared to the wild-type DspB enzyme.

In one embodiment and all the other embodiments of the invention, the invention provides an engineered enzymatically active T7 bacteriophage that expresses dispersin B enzyme (DspB) operably linked to a strong promoter, such as T7 φ10, wherein a nucleic acid sequence encoding a gene expanding or enhancing the infectivity and/or replication capacity of the T7 bacteriophage, such as T3 gene 1.2, is operably linked to a unique BclI site in the T7 phage and wherein the φ10-dspB construct is operably linked after the capsid gene 10B. In one embodiment, the T7 bacteriophage is T7SELECT415-1.

In one embodiment and all the other embodiments of the invention, the invention provides a method of dispersing bacterial biofilm comprising β-1,6-N-acetyl-D-glucosamine, the method comprising contacting the bacterial biofilm with a composition comprising an enzymatically active T7 bacteriophage that encodes and expresses dispersin B (DspB) operably linked to a strong promoter, such as T7 φ10, wherein a nucleic acid sequence encoding a gene expanding or enhancing the infectivity and/or expression range of the T7 bacteriophage, such as T3 gene 1.2 is operably linked into a unique BclI site in the T7 phage and wherein the φ10-dspB construct is operably linked after capsid gene 10B. In one embodiment, the biofilm is a mature biofilm. In one embodiment, the method comprises one time administration of about $10^2$, $10^3$, $10^4$, or $10^5$ PFU of the engineered enzymatially active bacteriophage.

In one embodiment, the invention provides an engineered lytic T7 bacteriophage comprising a nucleic acid encoding dispersin B operably linked to a strong promoter, such as T7 φ10 promoter and further comprising a nucleic acid encoding T3 1.2 gene, in one embodiment, the phage comprises SEQ ID NO: 9.

In one embodiment, and all the other embodiments of the invention, the administration is performed in vivo, into an animal, such as a human or livestock, wherein the engineered enzymatially active bacteriophage is administered alone or in a pharmaceutically acceptable carrier.

In one embodiment and all the other embodiments of the invention, one first diagnoses the bacterial infection in the animal, such as human or livestock, and then, based on the type of the bacterial infection, one selects a particular phage that is effective against the bacteria and the biofilm that the specific infecting bacteria produces. Bacterial cultures for diagnostic purposes are well known to one skilled in the art. Alternatively, one engineers a phage so that it effectively infects the bacterial strain that has infected the subject animal.

Similarly, a "diagnosis" step is also performed in certain embodiments, wherein other than living surfaces are treated with the methods of the invention. Accordingly, in one embodiment, one diagnoses the bacterium or bacteria infecting a surface, and then engineers a specific phage capable of infecting one or more of the bacteria present on said surface to encode an enzyme capable of digesting the specific biofilm produced by said bacterium or bacteria.

In one embodiment, animal diseases that are typically treated with antibiotics are treated with the methods of the present invention using an engineered phage. Particularly livestock, such as cows, pigs, chicken, sheep and horses are suitable target animals for the treatments of the present invention. Other animals can also be treated using the methods of the invention.

In one embodiment and all the other embodiments of the invention, the administration is performed into or onto non-living objects, such as water pipes, catheters, and other surfaces affected by bacteria and bacteria biofilm.

The administration of the enzymatically active bacteriophage can be performed before, after or concurrently with administration of other antibacterial agents, such as antibiotics and microbicides or agents capable of assisting in biofilm dispersion, such as chelating agents.

In one embodiment, the invention provides an engineered lytic T7 bacteriophage comprising a nucleic acid encoding dispersin B operably linked to T7 φ10 promoter and further comprising a nucleic acid encoding T3 1.2 gene. In one embodiment the nucleic acid encoding the phage comprises SEQ ID NO: 9. In one embodiment, the nucleic acid encoding the phage consists essentially of SEQ ID NO: 9. In one embodiment, the nucleic acid encoding the phage consists of SEQ ID NO: 9.

In another embodiment, the invention provides a method of dispersing bacterial biofilm comprising administering to a surface infected with biofilm an engineered lytic T7 bacteriophage comprising a nucleic acid encoding dispersin B operably linked to T7 φ10 promoter and further comprising a nucleic acid encoding T3 1.2 gene or another gene enhancing or expanding the phage infectivity range.

In one embodiment, the biofilm is a mature biofilm.

In one embodiment, the biofilm comprises β-1,6-N-acetyl-D-glucosamine.

In one embodiment, the method of dispersing bacterial biofilms further comprising a step of prior to administering the bacteriophage, determining if the biofilm comprises β-1,6-N-acetyl-D-glucosamine, and if it does, then administering the engineered lytic bacteriophage.

In one embodiment, the biofilm is formed by *Staphylococcus* and *E. coli*, including *E. coli* K-12, as well as clinical isolates of *E. coli*. In one embodiment, one first determines, by culturing bacterial sample from the subject or surface, if the subject carries *Staphylococcus* and *E. coli*, including *E. coli* K-12, as well as clinical isolates of *E. coli*. If the subject is determined to carry at least one of these bacterial strains, the phage of the invention is administered to the subject or surface.

In one embodiment, wherein the administering is performed once.

In one embodiment, the administering is performed before, after or concurrently with an antibiotic or antimicrobial agent.

In one embodiment, the administering is performed before, after or concurrently with a biofilm degrading chemical.

BRIEF DESCRIPTION OF DRAWINGS

FIG. 2A shows the genome of T7SELECT415-1 shows a unique BclI site and capsid gene 10B. FIG. 2B shows a DspB-expressing phage T7DspB was created by cloning T3 gene 1.2 into the unique BclI site and cloning the φ10-dspB construct after capsid gene 10B. FIG. 2C shows a non-DspB-expressing control phage T7control was created by cloning T3 gene 1.2 into the unique BclI site and cloning the control S•Tag insert (included in the T7SELECT415-1 kit) as a fusion with the capsid gene 10B.

FIG. 3A shows a mean absorbance (600 nm) for n=16 biofilm pegs stained with 1% CV, solubilized in 33% acetic acid, and diluted 1:3 in 1×PBS (50). FIG. 3B shows mean cell densities ($\log_{10}$(CFU/peg)) for n=12 biofilm pegs. Pegs treated with T7DspB resulted in a 3.65 $\log_{10}$(CFU/peg) reduction in viable cells recovered from *E. coli* biofilm compared to untreated biofilm. FIG. 3C shows mean phage counts ($\log_{10}$ (PFU/peg)) recovered from media in n=3 microtiter plate wells (wells) or sonication of n=3 biofilm pegs (biofilm), as indicated, after 24 h of treatment with initial inoculations of $10^3$ PFU/well. Both T7control and T7DspB showed evidence of replication with phage counts obtained from the microtiter plate wells or with phage counts recovered from the biofilms after sonication.

FIG. 4A shows a time course (up to 48 h) of viable cell counts for no treatment (red squares), treatment with T7control (black circles), or treatment with T7DspB (blue crosses) demonstrates that T7DspB significantly reduced biofilm levels compared with T7control. FIG. 4B shows an SEM image of T7DspB-treated biofilm after 20 h shows significant disruption of the bacterial biofilm. FIG. 4C shows an SEM image of untreated biofilm after 20 h shows a dense biofilm. FIG. 4D shows a time course of phage counts obtained after initial inoculation of *E. coli* TG1 biofilm with 103 PFU/well of T7control (circles) or T7DspB (crosses). Both T7control and T7DspB began to replicate rapidly after initial inoculation. FIG. 4E shows dose response curves of mean cell densities (measured after 24 h of treatment) for T7control (circles) and T7DspB (crosses). For all initial phage inoculations, T7DspB-treated biofilm had significantly lower mean cell densities compared to T7control-treated biofilm. FIG. 4F shows dose response curves of mean phage counts (measured after 24 h of treatment) for T7control (circles) and T7DspB (crosses). For all initial phage inoculations, both T7control and T7DspB multiplied significantly.

DETAILED DESCRIPTION OF THE INVENTION

Figure 1:
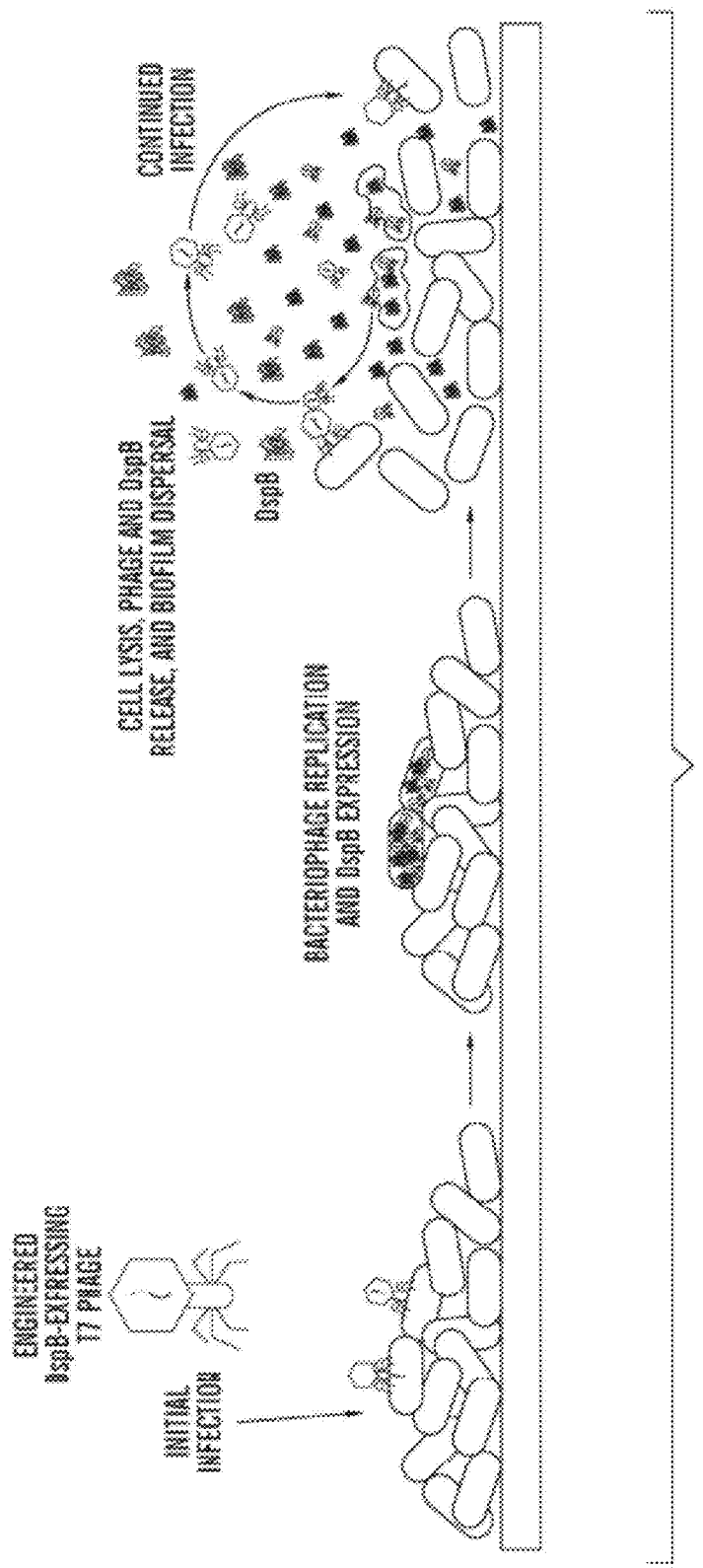
FIG. 1 shows a two-pronged attack strategy for biofilm removal with enzymatically-active DspB-expressing T7DspB phage. Initial infection of *E. coli* biofilm results in rapid multiplication of phage and expression of DspB. Both phage and DspB are released upon lysis, leading to subsequent infection as well as degradation of the crucial biofilm EPS component, β-1,6-N-acetyl-D-glucosamine (22).

The present invention provides engineered enzymatically active bacteriophages and their use for efficiently destroying bacteria and bacterial biofilms, particularly bacterial biofilms that comprise β-1,6-N-acetyl-D-glucosamine. In one preferred embodiment methods of destroying or eradicating a mature biofilm and bacteria therein are provided. The methods of the present invention provide at least two orders of magnitude greater efficiency in destruction of bacterial biofilms than any previously known phage-based method that we are aware of.

We engineered bacteriophage with biofilm-degrading enzymatic activity to create a synthetic biology platform for eradicating bacterial biofilms.

The bacteriophage can be any phage that has the capacity to infect a biofilm producing bacterium, such as *E. coli*, *P. aeriginosa*, *S. aureus*, *E. fecalis* and the like. Such phages are well known to one skilled in the art, and include, but are not limited to, lambda phages, T7, T3, and T-even and T-even like phages, such as T2, and T4, and RB69; also phages such as Pf1, Pf4, *Bacteroides fragilis* phage B40-8 and coliphage MS-2 can be used. For example, lambda phage attacks *E. coli* by attaching itself to the outside of the bacteria and injecting its DNA into the bacteria. Once injected into its new host, the phage uses *E. coli*'s genetic machinery to transcribe its genes. Any of the known phages can be engineered to express a biofilm degrading enzyme on its surface, as described herein. Preferably, the bacteriophage is T7, more preferably T7SELECT415-1.

The bacteriophages of the present invention are engineered using the traditional methods of genetic engineering that are well known to one skilled in the art. Based on the description in this specification and sequences provided herein and any other sequences known to one skilled in the art, one can readily prepare and produce the phages of the invention. We used T7SELECT415-1 phage to provide an illustration of engineering the phages of the invention. However, the same principles can be used to create any other phage known to one skilled in the art, such as lambda phages, T3, and other T-odd and T-even like phages, such as T2, T4 and RB69; and Pf1, Pf4, *Bacteroides fragilis* phage B40-8 and coliphage MS-2 using the principles described throughout the specification.

In one embodiment, one prepares an engineered T7 phage by using the T7SELECT415-1 phage display system (NOVAGEN). The T7select phage is engineered to express DspB intracellularly during infection. The DspB gene can be cloned, for example, from *Actinobacillus actinomycetemcomitans* genomic DNA (ATCC #700685D) into, for example, pET-9a plasmid (NOVAGEN) under the control of the strong promoter, such as T7 φ10 promoter. In one embodiment, the DspB gene is cloned between the NdeI and BamHI sites, for example, using the forward primer 5' atataatc catatg aat tgt tgc gta aaa ggc aat tc 3' (SEQ ID NO: 1) and reverse primer 5' atatac ggatcc tca ctc atc ccc att cgt ct 3' (SEQ Id NO: 2). In one embodiment, a stop codon is placed in all three reading frames downstream of the T7SELECT415-1 10B capsid gene followed by the φ10-dspB construct, to allow strong expression of DspB by T7 RNA polymerase during infection (FIG. 2B). The φ10-dspB construct can be isolated, for example, by PCR with the primers 5' gTA AcT AA cgaaat-taat acgactcact atagg 3' (SEQ ID NO: 3) and 5' atataa cggccg c aagctt tca ctc atc ccc att cgt ct 3' (SEQ ID NO: 4)(stop codons in uppercase letters). The product can be used in a subsequent PCR reaction with the primers 5' tactc gaattc t TAA gTA AcT AA cgaaattaat acgactc 3'(SEQ ID NO: 5) and 5' atataa cggccg c aagctt tca ctc atc ccc att cgt ct 3' (SEQ ID NO: 6) to create a construct beginning with stop codons in each reading frame followed by the φ10-dspB construct. Both the product of this PCR reaction and the T7SELECT415-1 DNA can be digested with EcoRI and EagI, purified, ligated together using T4 DNA ligase, and packaged into T7 phage particles with T7select packaging extracts to create phage T7DspB-precursor.

Since wild-type T7 is unable to replicate normally in F-plasmid-containing *E. coli*, in one embodiment, one can clone a gene that expands its host infectivity and/or replication capacity, such as gene 1.2 from phage T3 into T7DspB-precursor and T7control-precursor to create T7DspB and T7control, respectively, which are able to escape exclusion by the F plasmid (FIGS. 2B and 2C) (33). Genomic DNA from T7DspB-precursor and T7control-precursor is isolated, and T3 gene 1.2 can be cloned from the T3 genome, for example, using primers 5' cgta tgatca aacg agcagggcga acagtg 3' (SEQ ID NO: 7) and 5' cgta tgatca ccactc gttaaagtga ccttaaggat tc 3'(SEQ ID NO: 8) and inserted into the unique BclI site in both the T7DspB-precursor and T7control-precursor, which are then packaged with T7select packaging extracts. The resulting phage are amplified on *E. coli* BL21 and then plated on *E. coli* TG1(lacI::kan) to isolate T7DspB (FIG. 2B) and T7control (FIG. 2C).

Bacteria frequently live in biofilms, which are surface-associated communities encased in a hydrated EPS matrix, that is composed of polysaccharides, proteins, nucleic acids, and lipids and helps maintain a complex heterogeneous structure (8, 9). Biofilms constitute an essential and protective lifestyle for bacteria in many different natural and man-made environments, including dental plaques, water pipes, medical devices, and industrial systems (10).

Bacterial biofilms have been implicated as a source of persistent infection and contamination in medical, industrial, and food processing settings due to inherent resistance to antimicrobial agents and host defenses (8, 11-13). Thus, there exists a growing need for novel and effective treatments targeted at biofilms, particularly in light of the continually-worsening problem of antibiotic resistance and the discovery that antibiotic use can even induce biofilm formation (14, 15).

Accordingly, in one embodiment, the present invention provides a method for eradicating bacteria and bacterial biofilm comprising administering to a surface affected with bacterial biofilm an enzymatically active lytic bacteriophage that has been engineered to express an enzyme capable to degrading at least β-1,6-N-acetyl-D-glucosamine.

In one embodiment, the bacteriophage further expresses at least one enzyme selected from the group consisting of enzymes listed in Table A (Xavier et al. Microbiology 151 (2005), 3817-3832).

TABLE A

| Agent | Origin | Substrate | Notes/action | Reference |
|---|---|---|---|---|
| | | Enzymes | | |
| Polysaccharide depolymerase | Bacteriophage | *Enterobacter agglomerans* GFP in monospecies biofilms and in dual-species biofilms with *Klebsiella pneumoniae* G1 | Phage glycanases are very specific. Action of enzyme was observed when added to the phage-susceptible monospecies biofilm, leading to substantial biofilm degradation (Hughes et al., 1998) A 60 min treatment with a polysaccharase caused a 20% reduction in dual-species biofilm adhesion (Skillman et al., 1999) | |

TABLE A-continued

| Agent | Origin | Substrate | Notes/action | Reference |
|---|---|---|---|---|
| Alginate lyase, See, e.g., sequences with the following database entries O50660, ALGL_AZOCH; O52195, ALGL_AZOVI; Q9ZNB7, ALGL_HALMR; A6V1P7, ALGL_PSEA7; Q02R18, ALGL_PSEAB; Q06749, ALGL_PSEAE; Q1I563, ALGL_PSEE4; Q4KHY5, ALGL_PSEF5; P59786, ALGL_PSEFL; Q3KHR0, ALGL_PSEPF; B0KGQ9, ALGL_PSEPG; Q88ND1, ALGL_PSEPK; Q887Q5, ALGL_PSESM; Q9L7P2, ALGL_PSESY; Q4ZXL0, ALGL_PSEU2; P39049, ALXM_PHOS4; Q59478, ALYA_KLEPN; Q59639, ALYA_PSEAL; Q06365, ALYP_PSESO; | *Pseudomonas aeruginosa* | *Pseudomonas aeruginosa* alginate | Strains of *P. aeruginosa* overproducing alginate lyase detached at a higher rate than wild-type | Boyd & Chakrabarty (1994), Appl Environ Microbiol 60, 2355-2359. |
| | | | However, other studies showed that addition of alginate lyase to established *P. aeruginosa* biofilm caused no observable detachment (Christensen et al., 2001) | |
| Disaggregatase enzyme, see, e.g., sequences of dag of three *M. mazei* strains that are available from the DDBJ database. The Accession nos. are AB036793 (S-6T), AB052161 (TMA) and AB052162 (LYC) | *Methanosarcina mazei* | *Methanosarcina mazei* heteropolysaccharide capsule mediating cell aggregation | Conditions that are generally unfavourable for growth are associated with disaggregatase activity | Xun et al. (1990), Appl Environ Microbiol 56, 3693-3698 |
| Esterases with wide specificity | Wide range of bacteria | Acyl residues from bacterial polymers as well as other esters | Acetyl residues from intracellular carboxylesterase (EC 3.1.1.1) isolated from *Arthrobacter viscosus* removed acetyl residues from xanthan, alginate, glucose pentaacetate, cellobiose octaacetate, exopolysaccharide produced by *A. viscosus*, deacetylated p-nitrophenyl propionate, naphthyl acetate, isopropenyl acetate and triacetin (Cui et al., 1999) Esterases could alter the physical properties of a biofilm structure | Sutherland (2001), Microbiology 147, 3-9 |

TABLE A-continued

| Agent | Origin | Substrate | Notes/action | Reference |
|---|---|---|---|---|
| Dispersin B (or DspB), see, e.g., SEQ ID NO: 11 | *Actinobacillus actinomycetemcomitans* | Poly-β-1,6-GlcNAc implicated as an adhesion factor for biofilms of several bacterial species | Causes detachment of cells from *A. actinomycetemcomitans* biofilms and disaggregation of clumps of *A. actinomycetemcomitans* in solution (Kaplan et al., 2003) Treatment of *S. epidermidis* biofilms with dispersin B causes dissolution of the EPS matrix and detachment of biofilm cells from the surface (Kaplan et al., 2004) Disrupts biofilm formation by *E. coli*, *S. epidermidis*, *Yersina pestis* and *Pseudomonas fluorescens* (Itoh et al., 2005) | |
| DNase I, see, e.g., P00639, DNAS1_BOVIN; Q767J3, DNAS1_CANFA; Q9YGI5, DNAS1_CHICK; Q4AEE3, DNAS1_HORSE; P24855, DNAS1_HUMAN; P49183, DNAS1_MOUSE; O42446, DNAS1_OREMO; P11936, DNAS1_PIG; O18998, DNAS1_RABIT; P21704, DNAS1_RAT; P11937, DNAS1_SHEEP; P26295, DRN1_STREQ; P57487, END1_BUCAI; Q89AD7, END1_BUCBP; P25736, END1_ECOLI; P07059, END2_BPT4; | Commercial (Sigma-Aldrich) | Extracellular DNA in *Pseudomonas aeruginosa* biofilms | DNase affects the capability of *P. aeruginosa* to form biofilms when present in the initial development stages. Established biofilms were only affected to a minor degree by the presence of DNase | Whitchurch et al. (2002), Science 295, 1487 |
| Mixtures of enzymes | Commercial | *S. aureus*, *S. epidermidis*, *P. fluorescens* and *P. aeruginosa* biofilms on steel and polypropylene substrata | Pectinex UltraSP (Novo Nordisk A/S, a multicomponent enzyme preparation) reduced the number of bacterial cells in biofilms on stainless steel without any significant bactericidal activity (the activity of Pectinex Ultra is mainly a degradation of extracellular polysaccharides) | Johansen et al. (1997), Appl Environ Microbiol 63, 3724-3728 |
| | | *S. mutans*, *Actinomyces viscosus* and *Fusobacterium nucleatum* biofilms on saliva-coated hydroxyapatite | Mutanase and dextranase were shown to remove oral plaque from hydroxyapatite, but were not bactericidal (Novo Nordisk A/S) | |

Example of a dispersin B gene can be found, for example, with a database accession number ACCESSION AY228551; VERSION: AY228551.1, GI:30420959, see Sequence ID NO: 11 below:

```
   1 aattgttgcg taaaaggcaa ttccatatat ccgcaaaaaa caagtaccaa gcagaccgga
  61 ttaatgctgg acatcgcccg acatttttat tcacccgagg tgattaaatc ctttattgat
 121 accatcagec tttccggcgg taattttctg cacctgcatt tttccgacca tgaaaactat
 181 gcgatagaaa gccatttact taatcaacgt gcggaaaatg ccgtgcaggg caaagacggt
 241 atttatatta atccttatac cggaaagcca ttcttgagtt atcggcaact tgacgatatc
 301 aaagcctatg ctaaggcaaa aggcattgag ttgattcccg aacttgacag cccgaatcac
 361 atgacggcga tctttaaact ggtgcaaaaa gacagagggg tcaagtacct tcaaggatta
 421 aaatcacgcc aggtagatga tgaaattgat attactaatg ctgacagtat tacttttatg
 481 caatctttaa tgagtgaggt tattgatatt tttggcgaca cgagtcagca ttttcatatt
 541 ggtggcgatg aatttggtta ttctgtggaa agtaatcatg agtttattac gtatgccaat
 601 aaactatcct acttttttaga gaaaaaggg ttgaaaaccc gaatgtggaa tgacggatta
 661 attaaaaata cttttgagca aatcaacccg aatattgaaa ttacttattg gagctatgat
 721 ggcgatacgc aggacaaaaa tgaagctgcc gagcgccgtg atatgcgggt cagtttgccg
 781 gagttgctgg cgaaaggctt tactgtcctg aactataatt cctattatct ttacattgtt
 841 ccgaaagctt caccaacctt ctcgcaagat gccgcctttg ccgccaaaga tgttataaaa
 901 aattgggatc ttggtgtttg ggatggacga aacaccaaaa accgcgtaca aaatactcat
 961 gaaatagccg gcgcagcatt atcgatctgg ggagaagatg caaaagcgct gaaagacgaa
1021 acaattcaga aaaacacgaa aagtttattg gaagcggtga ttcataagac gaatggggat
1081 gagtga
```

Bacteriophage treatment has been proposed as one method for controlling bacterial biofilms (16). Phage have been used since the early 20th century to treat bacterial infections, especially in Eastern Europe, and have been shown to decrease biofilm formation (16, 17). For example, phage T4 can infect and replicate within *E. coli* biofilms and disrupt biofilm morphology by killing bacterial cells (18-20). Phage have also been modified to extend their natural host range. *E. coli* which produce the K1 polysaccharide capsule are normally resistant to infection by T7, but are susceptible to T7 that have been designed to express K1-5 endosialidase (21). Enzymatic degradation of EPS components is another useful strategy for disrupting biofilms, though bacterial cells are not killed (8, 22, 23). For instance, enzymatic degradation of a cell-bound EPS polysaccharide adhesin known as polymeric β-1,6-N-acetyl-D-glucosamine (PGA) by exogenously-applied dispersin B (DspB) has been demonstrated to reduce biofilms of several different species of bacteria (22).

DspB, an enzyme which is produced by *Actinobacillus actinomycetemcomitans*, hydrolyzes PGA, a crucial adhesin needed for biofilm formation and integrity in *Staphylococcus* and *E. coli*, including *E. coli* K-12 as well as clinical isolates (22). Reports of natural lytic phage with phage-borne polysaccharide depolymerases have shown that phage-induced lysis and EPS degradation are used in combination in natural systems to reduce bacterial biofilms (24, 25). These depolymerases appear to be carried on the surfaces of phage and degrade bacterial capsular polysaccharides to allow access to bacterial cell surfaces (24). However, the chance that one can isolate a natural phage that is both specific for the bacteria to be targeted and expresses a relevant EPS-degrading enzyme is likely to be low (26).

We engineered T7, an *E. coli*-specific phage (29, 30), to express DspB intracellularly during infection so DspB would be released into the extracellular environment upon cell lysis (FIG. 1).

Figure 2A:
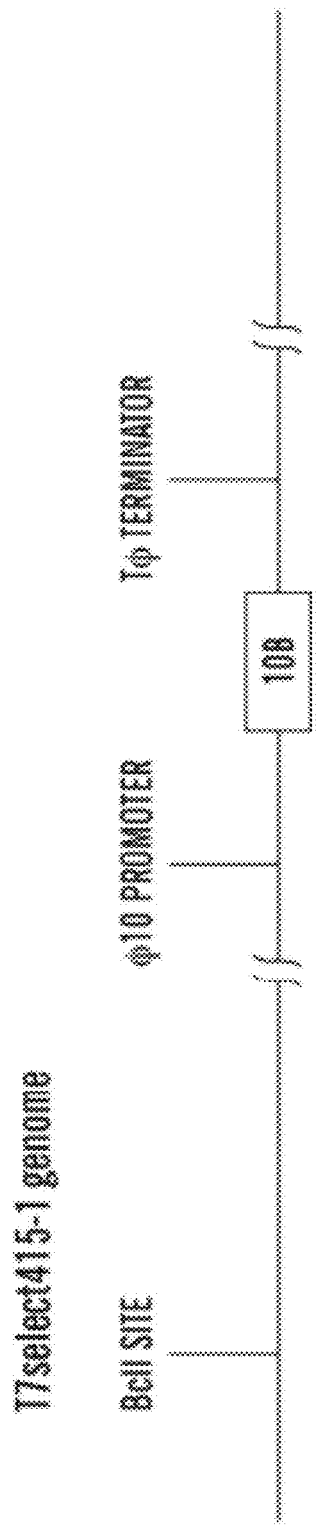
FIGS. 2A-2C show genomes of engineered phage used for biofilm treatment.
Figure 2B:
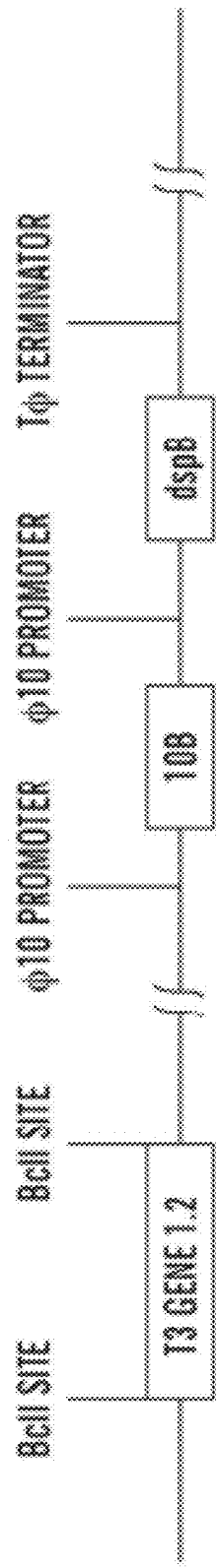
Figure 2C:
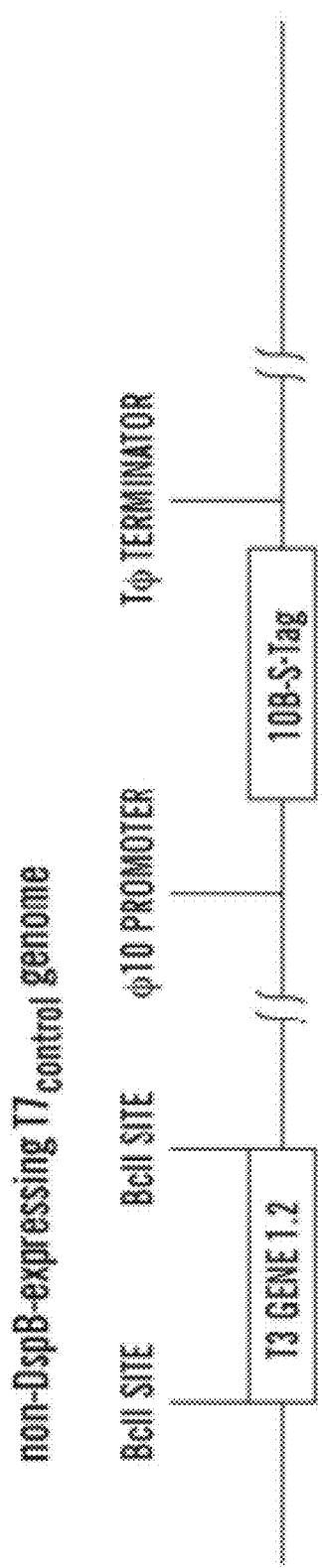

We employed a modified T7 strain (NOVAGEN T7SELECT415-1) with several deletions of nonessential genes (FIG. 2A). We cloned the gene coding for DspB (dspB) under the control of the strong T7 φ10 promoter so dspB would be strongly transcribed by T7 RNA polymerase during infection (FIG. 2B). As a control, we cloned an S•Tag insert into the T7 genome so that no DspB would be produced (FIG. 2C).

Accordingly, in one embodiment, the invention provides an engineered T7 *E. coli*-specific phage, for example T7SELECT415-1 phage, that comprises a nucleic acid encoding dispersin B (DspB) that is expressed intracellularly during phage infection of *E. coli*, wherein the nucleic acid encoding DspB is operably linked to a strong promoter, such as a T7 φ10 promoter, and wherein the T7 phage is engineered to further encode a gene that enhances and/or expands its infectivity and/or replication capacity, such as T3 gene 1.2. The sequences for the genes are well known to one skilled in the art and readily available from the publicly available databases.

To test the effectiveness of our engineered phage against pre-grown, mature biofilm, we cultivated *E. coli* TG1(lacI::kan) biofilms in LB media on plastic pegs using the standardized MBEC biofilm cultivation system. We used *E. coli* TG1 as the target biofilm strain since TG1 forms a thick, mature biofilm and contains the F plasmid (31). The F plasmid enhances biofilm maturation along with other biofilm-promoting factors in *E. coli*, including PGA, flagellum, cellulose, curli, antigen 43, and other conjugative pili and cell surface adhesins (31, 32). Because T7 is unable to replicate efficiently in F-plasmid-containing *E. coli*, gene 1.2 from T3 phage was also cloned into the unique BclI site in our engineered T7 phage and control T7 phage to circumvent F-plasmid-mediated exclusion and extend the phage host range (FIGS. 2B and 2C) (33). The control phage and engineered phage were named T7control and T7DspB, respectively (FIGS. 2B and 2C).

Figure 3A:
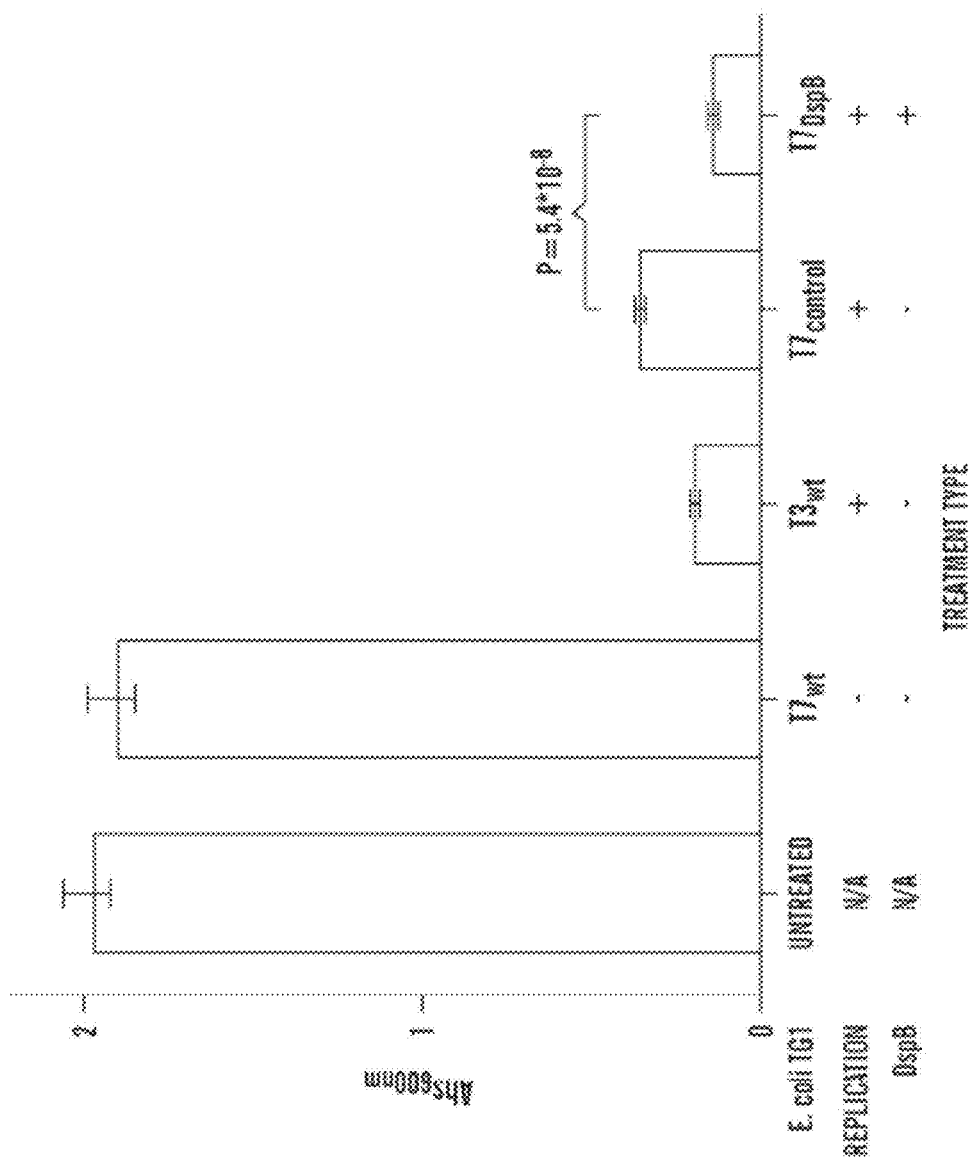
FIGS. 3A-3C show assays for *E. coli* TG1 biofilm levels and phage counts after 24 h with no treatment or with treatment with wild-type phage T7wt, wild-type phage T3wt, non-DspB-expressing control phage T7control, or DspB-expressing phage T7DspB. Error bars indicate s.e.m.

To determine whether the T7DspB phage was more effective than the T7control phage, we first employed a crystal violet (CV) assay to assess the amount of biofilm on the pegs after phage treatment. Pre-grown TG1(lacI::kan) biofilm was inoculated with only LB media or infected with 103 plaque forming units per peg (PFU/peg) of T7control or T7DspB phage (FIG. 3A). To assess whether our engineered enzymatic phage was more efficacious than wild-type phage at attacking biofilm despite being made with a modified T7 phage, we also treated biofilm with wild-type T7 (T7wt) or wild-type T3 (T3wt) (FIG. 3A).

After 24 hours of treatment, CV staining of untreated biofilm had a 600 nm absorbance (A600) approximately equal to that for T7wt-treated biofilm (FIG. 3A). Both T3wt-treated biofilm and T7control-treated biofilm were reduced compared with the untreated biofilm: the former had an A600 that was lower than that of untreated biofilm by a factor of 10.3, while the latter had an A600 that was lower than that of untreated biofilm by a factor of 5.6 (FIG. 3A).

However, the amount of biofilm left on the T7DspB-treated pegs was significantly less than that with the non-enzymatic phage treatment types, with an A600 which was less by a factor of 14.5 than that of untreated biofilm and less by a factor of 2.6 than that of T7control-treated biofilm ($P=5.4*10^{-8}$).

These findings demonstrate that DspB expression in T7DspB is crucial to elevating its biofilm-removing efficacy over that of wild-type phage and non-enzymatic T7control phage (FIG. 3A).

Figure 3B:
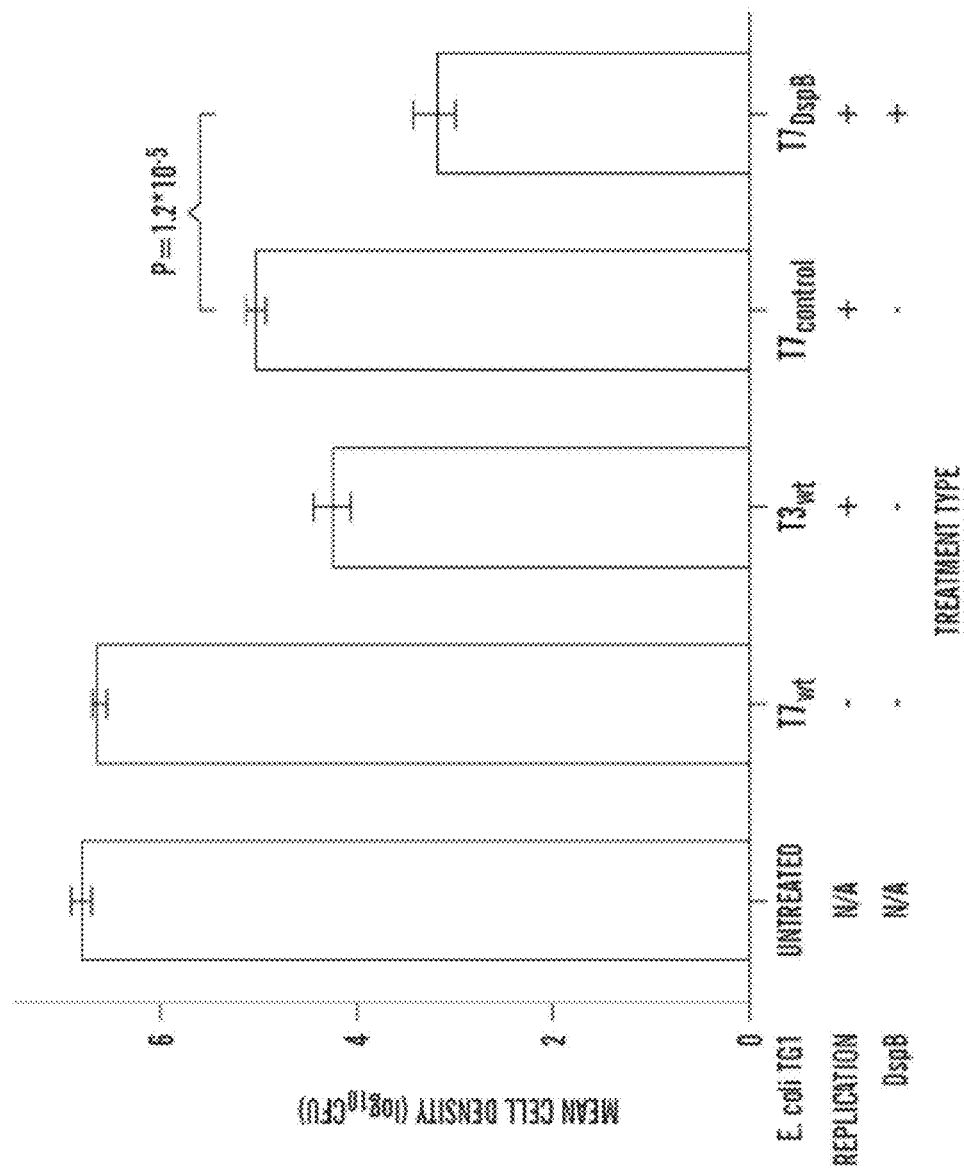

To confirm that the decrease in CV staining corresponded with killing of biofilm cells, we used sonication to obtain viable cell counts (CFU/peg) for bacteria surviving in the biofilms after phage treatment. Pre-grown TG1(lacI::kan) biofilm (prior to treatment) reached a mean cell density of 6.4 $\log_{10}$(CFU/peg) after 24 h of growth (FIG. 3B). After 24 h of additional growth in new LB media with no phage treatment, the untreated biofilm had a mean cell density of 6.9 $\log_{10}$ (CFU/peg) (FIG. 3B). T3wt-treated biofilm had a mean cell density that was less than that of T7control-treated biofilm by a factor of 5.9 and greater than that of T7DspB-treated biofilm by a factor of 12 (FIG. 3B). T7control-treated biofilm had a mean cell density of 5.1 $\log_{10}$(CFU/peg) while the mean cell density for T7DspB-treated biofilm was 3.2 $\log_{10}$(CFU/peg), the lowest of all the treatment types (FIG. 3B). The difference in viable cells recovered from T7control-treated biofilm and T7DspB-treated biofilm was statistically significant ($P=1.2*10^{-5}$). These results are consistent with our CV staining data and demonstrate that DspB-expressing T7DspB phage are substantially more effective at killing *E. coli* TG1 biofilm compared with wild-type T3wt, wild-type T7wt, and non-DspB-expressing control T7control phage.

Figure 3C:
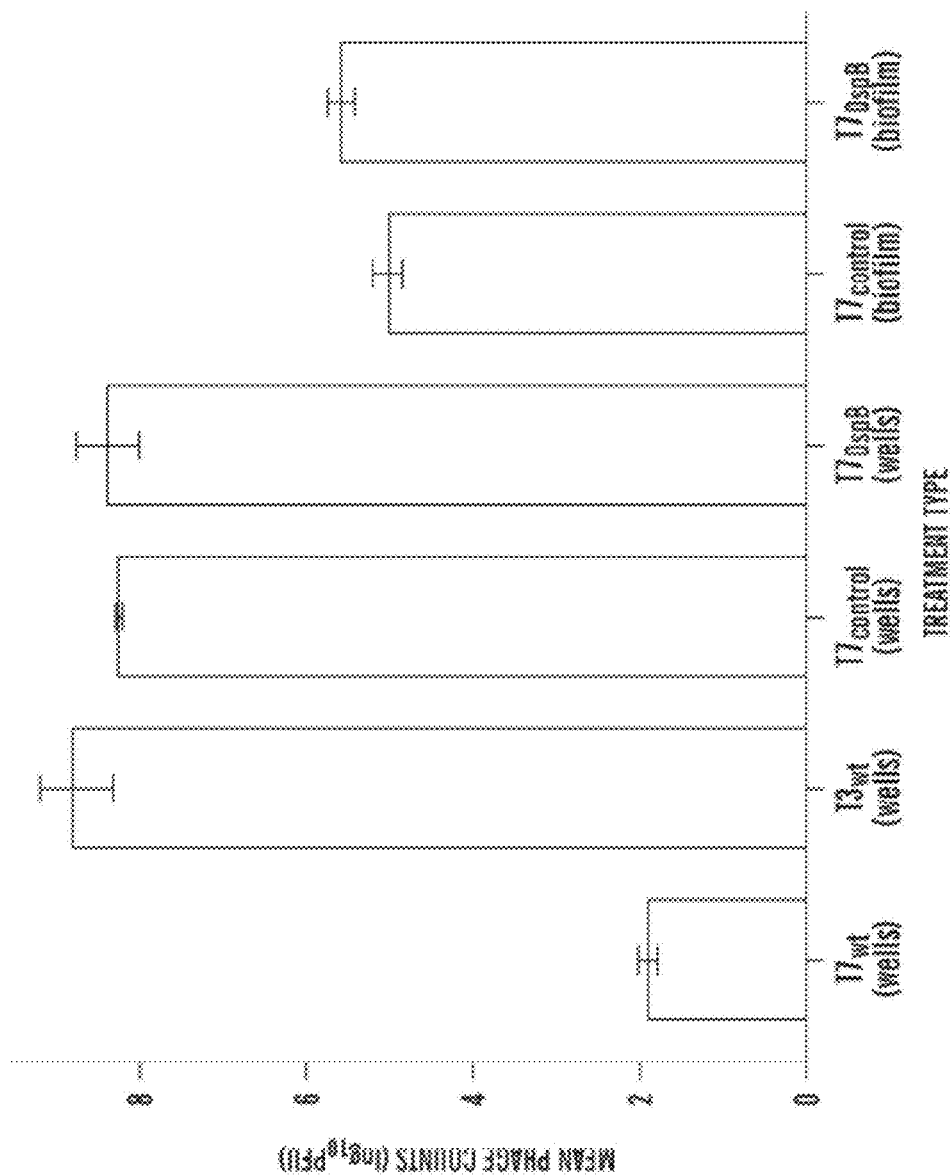

Our two-pronged method of biofilm eradication involves expression of DspB and rapid phage replication (FIG. 1). To confirm that our phage multiplied, we obtained PFU counts from media in the microtiter plate wells. By 24 h of treatment, wild-type T7 had not replicated but wild-type T3 had multiplied significantly within the biofilm (FIG. 3C). To compare the amount of phage in the microtiter plate wells with phage residing in the biofilms, we also obtained PFU counts by sonicating the biofilms. After 24 h of treatment, PFU counts for T7control and T7DspB recovered from the microtiter plate wells were several orders of magnitude greater than PFU counts recovered by sonication of the biofilms (FIG. 3C). Overall, PFU counts obtained from the wells and the biofilms were all orders of magnitude greater than the initial inoculation of 103 PFU, confirming that phage multiplication indeed took place (FIG. 3C).

Figure 4A:
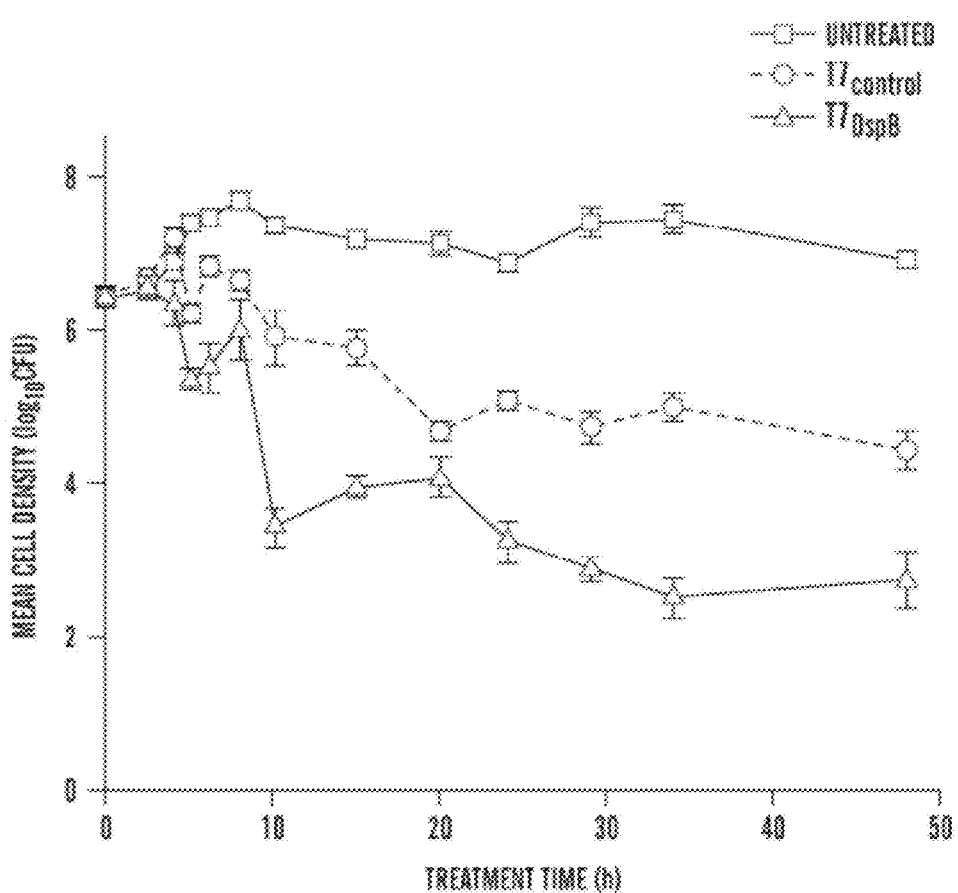
FIGS. 4A-4F show time-course curves, dosage response curves, and SEM images for engineered phage treatment targeting *E. coli* TG1 biofilm. Scale bars are 10 µm. Each data point in parts (A) and (E) represents the mean log 10-transformed cell density of n=12 biofilm pegs. Each data point in parts (D) and (F) represents the mean log 10-transformed phage counts obtained from n=3 microtiter plate wells. Error bars indicate s.e.m.

Accordingly, we determined that T7DspB had greater biofilm-removing capability than T7control after 24 h of infection. We also determined the time course of biofilm destruction. As shown in FIG. 4A, by 5 h post-infection, T7DspB-treated biofilm had a mean cell density that was 0.82 $\log_{10}$ (CFU/peg) less than T7control-treated biofilm ($P=2.0*10^{-4}$). At 10 h post-infection, T7DspB-treated biofilm began to settle at a steady-state mean cell density between 3 to 4 $\log_{10}$(CFU/peg), while T7control-treated biofilm flattened out at approximately 5 $\log_{10}$(CFU/peg) by 20 h post-infection (FIG. 4A).

T7DspB-treated biofilms had mean cell densities that were approximately two orders of magnitude lower than T7control-treated biofilms, up to 48 h of total treatment (FIG. 4A).

In addition, T7DspB treatment reduced biofilm levels by about 99.997% (4.5 $\log_{10}$(CFU/peg)) compared with untreated biofilm.

Further, we found no evidence of phage resistance developing over the long time course of treatment (FIG. 4A).

Figure 4B:
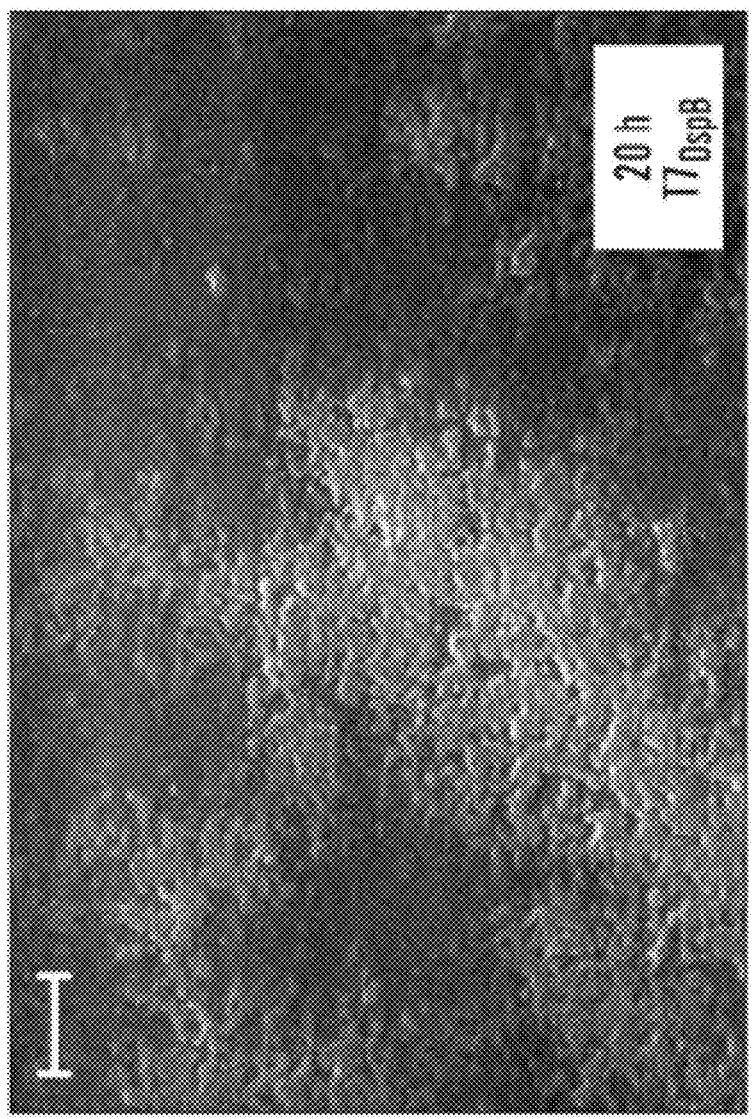
Figure 4C:
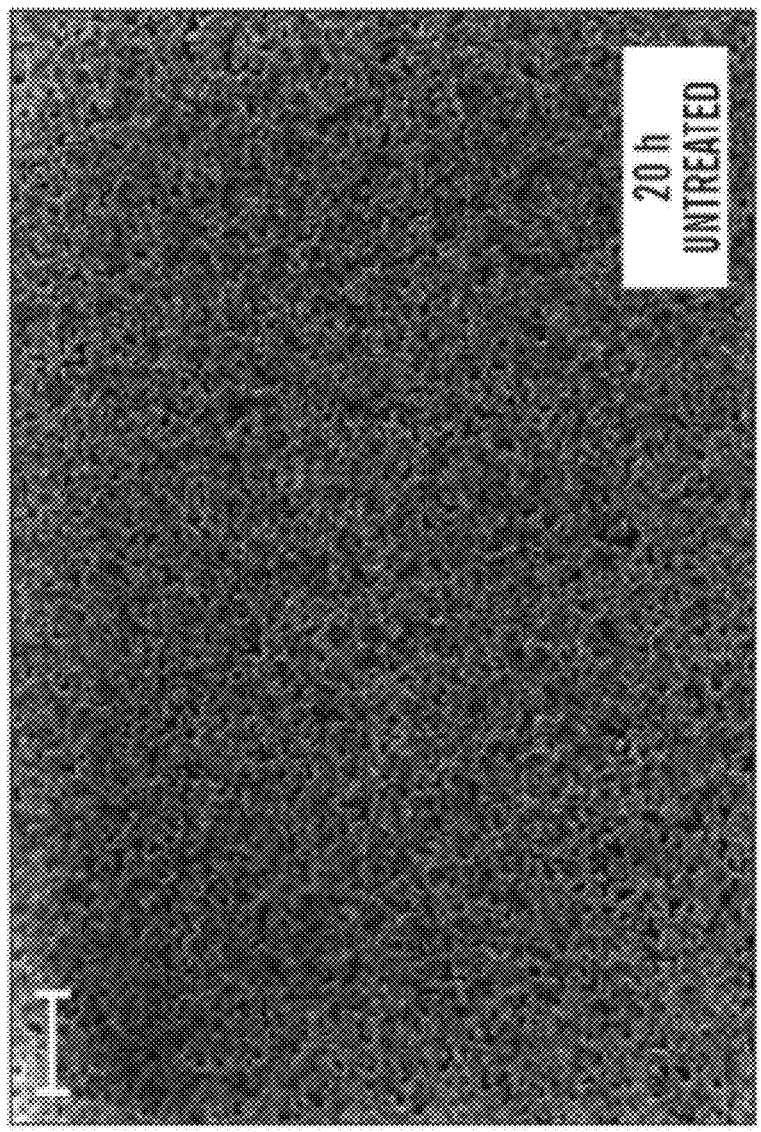

We also used scanning electron microscopy (SEM) to image the biofilm pegs over the time course of phage treatment in order to directly visualize biofilm dispersal by our enzymatically-active phage (FIG. 4B, FIG. 4C). After 20 h of treatment, T7DspB-treated biofilm (FIG. 4B) was significantly disrupted compared with the untreated biofilm (FIG. 4C).

These results confirm that T7DspB indeed causes both biofilm reduction and bacterial cell killing.

We studied scanning electron microscopy images for untreated, T7control-treated, and T7DspB-treated biofilms. Consistent with time-course data (FIG. 4A), T7DspB-treated biofilm and T7control-treated biofilm were indistinguishable from untreated biofilm at 2 h 25 min post-infection. However, by 4 h post-infection, T7DspB-treated biofilm began to lyse and disperse significantly, while T7control-treated biofilm was still largely undisturbed. By 10 h post-infection, significant amounts of cell debris were seen in both T7control-treated and T7DspB-treated biofilms. At 20 h post-infection, T7control-treated and T7DspB-treated biofilms had been disrupted by phage treatment, but T7DspB-treated biofilm was composed largely of cell debris and had fewer intact cells than T7control-treated biofilm.

Figure 4D:
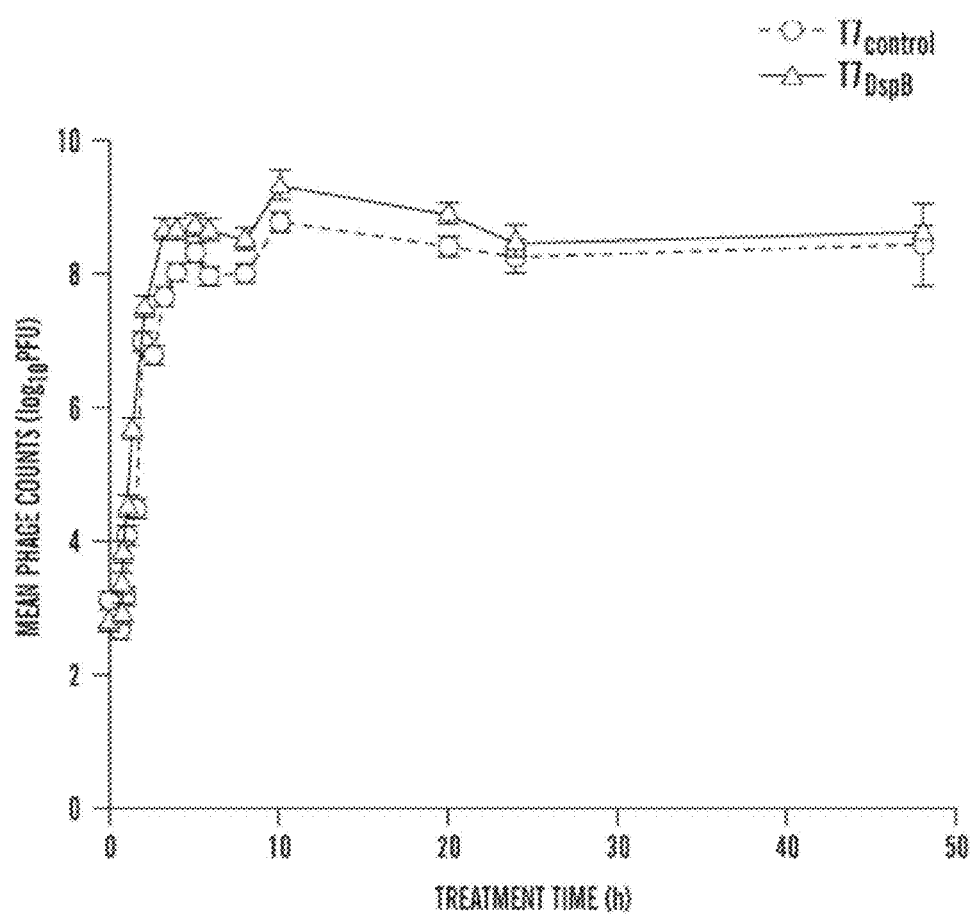

To verify that phage replication was occurring over time, we obtained PFU counts in the microtiter wells. As seen in FIG. 4D, both T7control and T7DspB began to replicate within the bacterial biofilm as early as 50 minutes post-infection. By about 190 minutes, T7control and T7DspB PFU/peg approached steady-state levels of approximately 8 to 9 $\log_{10}$ (PFU/peg), indicating that phage replication had occurred (FIG. 4D). T7DspB PFU/peg were generally higher than T7control PFU/peg but not by orders of magnitude as was the case for CFU counts per peg. This is because the T7 burst size (~250 PFU per infective center) (34) multiplied by the number of the extra cells killed by T7DspB, compared with T7control, equals extra PFU/peg that are insignificant compared with the PFU levels already reached by T7control. We did not note any significant differences in burst sizes and growth rates between T7DspB and T7control.

Considering that the above experiments were carried out with initial inoculations of $10^3$ PFU/peg, which translates to a multiplicity of infection (MOI) of about $1:10^{3.4}$ (FIG. 4A), we next determined the effect of changing the initial MOI on biofilm removal. With low phage doses, repeated rounds of phage multiplication and DspB expression should promote biofilm dispersal and allow more bacterial cells to be accessible for subsequent phage infection. With high phage doses, initial DspB production post-infection should also be very disruptive to biofilm integrity.

Figure 4E:
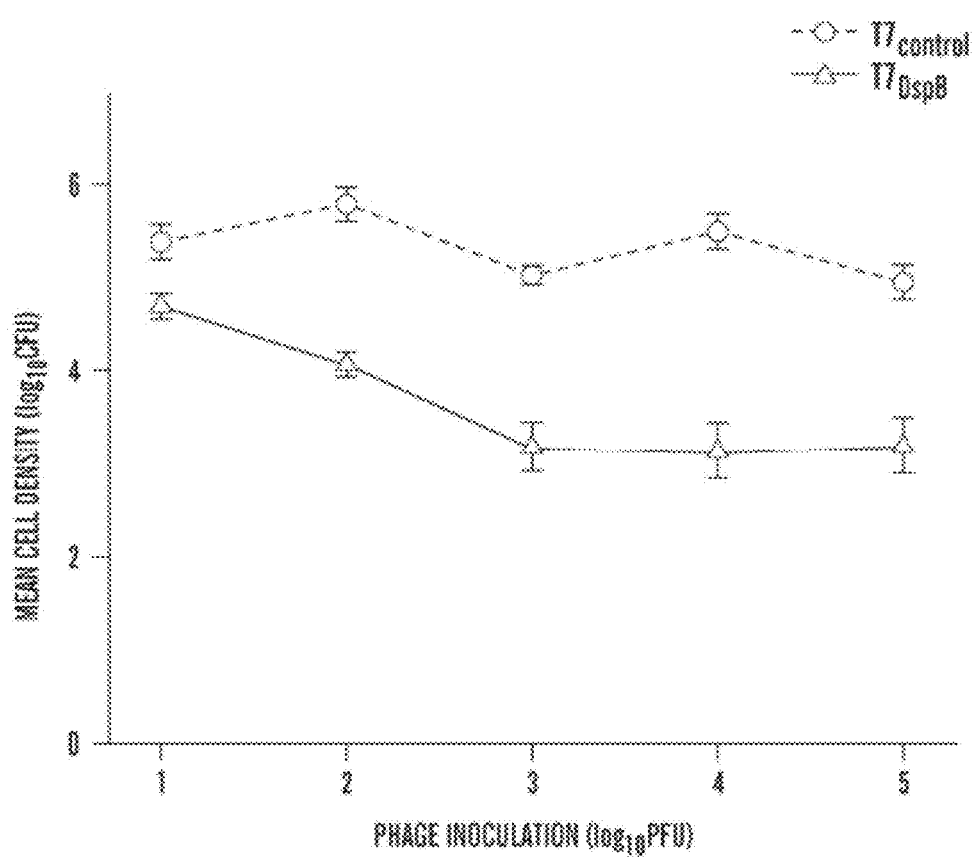

As shown in FIG. 4E, T7DspB was much more effective than T7control at removing biofilm at all inoculation levels tested, ranging from $10^1$ PFU/peg to $10^5$ PFU/peg. A dose-dependent effect of phage inoculation on biofilm destruction was observed, with larger inoculations leading to lower mean cell densities, particularly for T7DspB (FIG. 4E).

At inoculation levels greater than or equal to $10^2$ PFU/peg, mean cell densities (CFU/peg) for T7DspB-treated biofilm were significantly lower than those for T7control-treated biofilm by a factor of 49-232 (FIG. 4E).

Figure 4F:
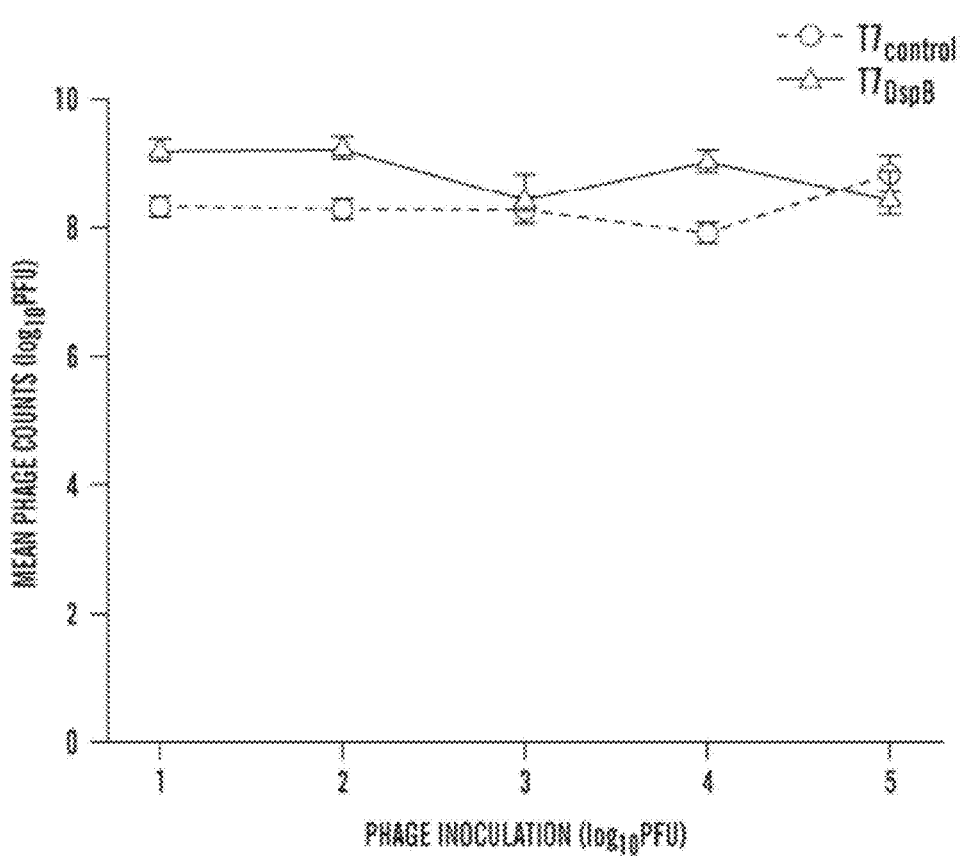

Thus, at low and high initial inoculations, DspB-expressing T7 is more efficacious at disrupting *E. coli* TG1 biofilm compared with non-DspB-expressing control T7. All phage dosages tested exhibited phage multiplication within the biofilm (FIG. 4F).

Without wishing to be bound by a theory, these results together show that DspB-expressing phage has significantly improved efficacy in real-world situations where the ability to deliver high levels of phage to biofilms may be limited or where sustained phage replication is less likely, e.g., in the gastrointestinal tract of cholera patients (35, 36).

Accordingly, we demonstrated that our novel engineered phage which express biofilm-degrading enzymes are more efficacious at removing bacterial biofilms than non-enzymatic phage alone. Therefore, we have described and taught a phage design that can be adapted to work in other phage and with other biofilm-degrading enzymes to target a wide range of biofilms.

Thus, engineered bacteriophage treatment provides a novel addition to the therapies or treatment methods available for use against bacterial biofilms in medical, industrial, and biotechnological settings (17).

In one embodiment, the bacteria to be targeted using the phage used in the methods of the invention include *E. coli, S. epidermidis, Yersina pestis* and *Pseudomonas fluorescens*.

The described phage system can also be designed to include directed evolution for optimal enzyme activity, delaying cell lysis or using multiple phage promoters to allow for increased enzyme production, targeting multiple biofilm EPS components with different proteins. One can also target multi-species biofilm with a cocktail of different species-specific engineered enzymatically-active phage, and use a combination therapy using the engineered phage of the invention and antibiotics or combinations thereof that are well known to one skilled in the art to improve the efficacy of both types of treatment.

The phages of the invention can also be used together with other antibacterial or biofilm degrading agents or chemicals such as EGTA, a calcium-specific chelating agent, effected the immediate and substantial detachment of a *P. aeruginosa* biofilm without affecting microbial activity, NaCl, $CaCl_2$ or $MgCl_2$, surfactans and urea.

Phage therapy has begun to be accepted in industrial and biotechnological settings. For example, the FDA recently approved the use of phage targeted at *Listeria monocytogenes* as a food additive (37). Despite the fact that phage therapy has several challenges that must be overcome before it will be accepted in Western medicine for treating humans (17), phage therapies have been used successfully in Eastern Europe for over 60 years. It has been shown, for example, that combination therapy with antibiotics and phage may alleviate the development of phage resistance (26, 36, 38). Long-circulating phage has been isolated that also avoids RES clearance to increase in vivo efficacy (35). Accordingly, the methods of the present invention are applicable to human and other animal treatment although clinical trials may be needed to establish their specific tolerance. However, our experiments have already shown that these methods are effective in dispersing biofilms, including biofilms present in human organs, such as colon or lungs.

The specificity of the phage for host bacteria is both an advantage and a disadvantage for phage therapy. Specificity allows human cells as well as innocuous bacteria to be spared, potentially avoiding serious issues such as drug toxicity or *Clostridium difficile* overgrowth that can arise with antibiotic use. *C. difficile* infection is characterized by diarrhea and colitis, and has increased in severity in recent years (42). Antibiotic therapy is believed to alter the microbial flora in the colon due to lack of target specificity, thus allowing *C. difficile* to proliferate and cause disease (43). Furthermore, the ability of our engineered phage to utilize the local bacterial synthetic machinery to produce biofilm-degrading enzymes means that exogenously-applied enzymes, which could have unintended effects on off-target biofilms, are not needed.

However, host specificity means that a well-characterized library of phage must be maintained so that an appropriate therapy can be designed for each individual infection (26). The diversity of bacterial infections implies that it may be difficult for any particular engineered phage to be a therapeutic solution for a wide range of biofilms. Accordingly, in one embodiment, the invention provides use of engineered enzymatically active phage cocktails that comprise at least two, three, four, five, 6, 7, 8, 9, 10 or even more different phages that have different hosts to cover wider a range of target bacteria. In one embodiment, at least one of the phages in the cocktail is an engineered lytic T7 bacteriophage comprising a nucleic acid encoding dispersin B enzyme operably linked to a T7 φ10 promoter and further comprising a nucleic acid encoding T3 1.2 gene. In one embodiment, at least one of the phages comprises a nucleic acid with SEQ ID NO: 9.

One skilled in the art can make a collection of enzymatically-active engineered phage by cost-effective, large-scale DNA sequencing and DNA synthesis technologies described and well known to one skilled in the art (see, e.g., 2, 4, 44). Sequencing technologies allows the characterization of collections of natural phage that have been used in phage typing and phage therapy for many years (45, 46). Accordingly, a skilled artisan can use synthetic technologies as described herein to add biofilm-degrading enzymes to produce new, modified phage.

Furthermore, rational engineering methods with new synthesis technologies can be employed to broaden phage host range. For example, T7 can be modified to express K1-5 endosialidase, allowing it to effectively replicate in *E. coli* that produce the K1 polysaccharide capsule (21). We took advantage of gene 1.2 from phage T3 to extend our phage host range to include *E. coli* that contain the F plasmid, thus demonstrating that multiple modifications of a phage genome can be done without significant impairment of the phage's ability to replicate (33). *Bordetella* bacteriophage use a reverse-transcriptase-mediated mechanism to produce diversity in host tropism which can also be used according to the methods of the present invention to create a phage that encodes a biofilm degrading enzyme, such as dispersin B, and is lytic to the target bacterium or bacteria (47, 48). In addition, utilizing enzymes, such as DspB, that target important adhesins which are common to a broad range of bacterial species, including clinical strains, allow enzymatically-active phage to be applicable to treatment of a greater number of infections (22). The many biofilm-promoting factors required by *E. coli* K-12 to produce a mature biofilm are likely to be shared among different biofilm-forming bacterial strains and are thus also targets for engineered enzymatic bacteriophage (32).

The enzymatically active bacteriophage of the invention can be formulated in combination with one or more pharmaceutically-acceptable anti-microbial agents. In this regard, combinations of different antimicrobial agents may be tailored to target different (or the same) microorganisms that contribute towards morbidity and mortality. The pharmaceutically acceptable anti-microbial agents of the present invention are suitable for internal administration to an animal, for example human. However, if the phage of the invention is to be used in industrial sterilizing, sterilizing chemicals such as detergents, disinfectants, and ammonium-based chemicals (e.g. quaternary ammonium compounds such as QUATAL) can be used in combination with, or prior to or after the treatment with the phage. Such sterilizing chemicals are typically used in the art for sterilizing industrial work surfaces (e.g. in food processing, or hospital environments), and are not suitable for administration to an animal.

Strong promoter useful according to the present invention are well known to a skilled artisan. Similarly, various genes that can enhance or expand the infectivity and/or replication range of a phage are well known to a skilled artisan.

The present invention also provides pharmaceutical compositions comprising an engineered lytic T7 bacteriophage comprising a nucleic acid encoding dispersin B operably linked to T7 φ10 promoter, e.g., a phage comprising a nucleic acid encoding SEQ ID NO: 9, and further comprising a nucleic acid encoding T3 1.2 gene, and a pharmaceutically acceptable excipient. Suitable carriers for the enzymatically active lytic phages of the invention, for instance, and their formulations, are described in Remington' Pharmaceutical Sciences, 16th ed., 1980, Mack Publishing Co., edited by Oslo et al. Typically an appropriate amount of a pharmaceutically acceptable salt is used in the formulation to render the formulation isotonic. Examples of the carrier include buffers such as saline, Ringer's solution and dextrose solution. The pH of the solution is preferably from about 5 to about 8, and more preferably from about 7.4 to about 7.8. Further carriers include sustained release preparations such as semipermeable matrices of solid hydrophobic polymers, which matrices are in the form of shaped articles, e.g. liposomes, films or microparticles. It will be apparent to those of skill in the art that certain carriers may be more preferable depending upon for instance the route of administration and concentration of the a enzymatically active bacteriophage being administered.

Administration to human may be accomplished by means determined by the underlying condition. For example, if the phage is to be delivered into lungs of an individual, inhalers can be used. If the composition is to be delivered into any part of the gut or colon, coated tablets, suppositories or orally administered liquids, tablets, caplets and so forth may be used. A skilled artisan will be able to determine the appropriate way of administering the phages of the invention in view of the general knowledge and skill in the art.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I-IV (D. M. Weir and C. C. Blackwell, eds.), 1986; Manipulating the Mouse Embryo, Cold Spring Harbor Laboratory Press, 1986.

The following Examples are provided to illustrate the present invention, and should not be construed as limiting thereof.

Some embodiments of the invention are provided in the following paragraphs:

1. An engineered lytic T7 bacteriophage comprising a nucleic acid encoding dispersin B enzyme or an β-1,6-N-acetyl-D-glucosamine degrading enzymatically active fragment thereof operably linked to a strong promoter and further comprising a nucleic acid encoding a gene to enhance or expand infectivity and or replication capacity of the lytic T7 bacteriophage.

2. The engineered lytic T7 bacteriophage of paragraph 1, wherein the nucleic acid encoding a gene to enhance or expand infectivity and or replication capacity of the lytic T7 bacteriophage encodes T3 1.2 gene.

3. The engineered lytic T7 bacteriophage of paragraphs 1 or 2, wherein the strong promoter is T7 φ10.

4. A method of dispersing bacterial biofilm comprising administering to a surface infected with biofilm the method comprising administering to the surface an engineered lytic T7 bacteriophage comprising a nucleic acid encoding dispersin B enzyme or an β-1,6-N-acetyl-D-glucosamine degrading enzymatically active fragment thereof operably linked to a strong promoter and further comprising a nucleic acid encoding a gene to enhance or expand infectivity and or replication capacity of the lytic T7 bacteriophage.

5. The method of paragraph 4, wherein the nucleic acid encoding a gene to enhance or expand infectivity and or replication capacity of the lytic T7 bacteriophage encodes T3 1.2 gene.

6. The method of paragraphs 4 or 5, wherein the strong promoter is T7 φ10.

7. The method of paragraph 4, wherein the biofilm is a mature biofilm.

8. The method of paragraph 4, wherein the biofilm comprises β-1,6-N-acetyl-D-glucosamine.

9. The method of paragraph 8 further comprising a step of prior to administering the bacteriophage, determining if the biofilm comprises β-1,6-N-acetyl-D-glucosamine, and if it does, then administering the engineered lytic bacteriophage.

10. The method of paragraph 4, wherein the biofilm is formed by bacteria selected from the group consisting of *Staphylococcus* and *E. Coli*, including *E. Coli* K-12 strain, and clinical isolates of *E. coli*.

11. The method of paragraph 4, wherein the administering is performed once.

12. The method of paragraph 4, wherein the administering is performed before, after or concurrently with an antibiotic or antimicrobial agent.

13. The method of paragraph 4, wherein the administering is performed before, after or concurrently with a biofilm degrading chemical.

EXAMPLES

Bacterial strains, bacteriophage, and chemicals. *E. coli* TG1 (F'traD36 lacIqΔ(lacZ) M15 proA+B+/supE Δ(hsdM-mcrB)5 (rk- mk- McrB-) thi Δ(lac-proAB)) was obtained from Zymo Research (Orange, Calif.). The strain TG1 (lacI::kan) used to grow biofilm was created by one-step inactivation of the lacI gene by a kanamycin-resistance cassette (49). *E. coli* BL21 was obtained from NOVAGEN Inc. (San Diego, Calif.). Wild-type T7 (ATCC #BAA-1025-B2) and T3 (ATCC #11303-B3) were purchased from ATCC (Manassas, Va.). Standard chemicals were obtained from sources as described in Supporting Methods.

Construction and purification of engineered phage. Our engineered T7 phage was created using the T7SELECT415-1 phage display system (NOVAGEN) with standard molecular biology techniques. Instead of cloning DspB onto the phage surface, we designed the T7select phage to express DspB intracellularly during infection. The dspB gene was cloned from *Actinobacillus actinomycetemcomitans* genomic DNA (ATCC #700685D) under the control of the strong T7 φ10 promoter downstream of the T7SELECT415-1 10B capsid gene and stop codons in all three reading frames to create T7DspB-precursor (FIG. 2B). Packaging of the modified genome was done with the T7select packaging extracts. The control phage, T7control-precursor, was constructed by cloning the T7select control S•Tag insert into the T7SELECT415-1 genome (FIG. 2C). Since wild-type T7 cannot replicate normally in F-plasmid-containing *E. coli*, we cloned gene 1.2 from phage T3 into the unique BclI site in T7DspB-precursor and T7control-precursor to create T7DspB and T7control, respectively, which are able to escape exclusion by the F plasmid (FIGS. 2B and 2C) (33). The resulting phage were amplified on *E. coli* BL21 and plated on *E. coli* TG1 (lacI::kan) to isolate T7DspB (FIG. 2B) and T7control (FIG. 2C), which were confirmed by PCR to have T3 gene 1.2.

Prior to biofilm treatment, T7DspB and T7control were amplified on *E. coli* BL21 and purified. 12 mL of BL21 overnight cultures were diluted with 12 mL of LB in 125 mL flasks, inoculated with 30 µL of high-titer phage stock, and allowed to lyse at 37° C. and 300 rpm for 3 h. Lysed cultures were clarified by centrifuging for 10 minutes at 10,000 g and filtering the supernatants through NALGENE #190-2520 0.2 µm filters (Nalge Nunc International, Rochester, N.Y.). The purified solutions were centrifuged in a Beckman SW.41T rotor for 1 h at 29,600 rpm to concentrate the phage. The supernatants were removed and pellets were resuspended in 0.2 M NaCl, 2 mM Tris-HCl pH 8.0, and 0.2 mM EDTA. Phage suspensions were reclarified in tabletop microcentrifuges at maximum speed (~13,200 rpm) for 10 minutes. The purified supernatants were finally diluted in 0.2 M NaCl, 2 mM Tris-HCl pH 8.0, and 0.2 mM EDTA for treatment. Appropriate amounts of phage were added to LB+kanamycin (30 µg/mL) for treatment, as described below. Phage purified by this protocol were no more effective at reducing bacterial biofilm levels compared with phage purified by centrifugation with CsCl step gradients.

All phage PFU counts were determined by combining phage with 300 µL of overnight *E. coli* BL21 culture and 4-5 mL of 50° C. LB top agar (0.7% w/v agar). This solution was mixed thoroughly, poured onto LB agar plates, inverted after hardening, and incubated for 4-6 h at 37° C. until plaques were clearly visible.

Biofilm growth and treatment. All experiments were performed in LB media+kanamycin (30 µg/mL). *E. coli* biofilms were grown with the MBEC Physiology & Genetics Assay (MBEC BioProducts Inc., Edmonton, Canada), which consists of a 96-peg lid that fits into a standard 96-well microtiter plate. Each well was inoculated with 150 µL of media containing 1:200 dilutions of overnight cultures which had been grown at 37° C. and 300 rpm. Control wells with only media but no bacteria were included. MBEC lids were placed in the microtiter plates, inserted into plastic bags to prevent evaporation, and placed in a shaker (HT Infors MINITRON) for 24 h at 35° C. and 150 rpm to form biofilm on the pegs.

For all treatments except for the dose response experiment, 10³ PFU of phage were combined with 200 µL LB+kanamycin (30 µg/mL) in each well in new microtiter plates (COSTAR #3370). For the dose response experiment, 10¹, 10², 10³, 10⁴, or 10⁵ PFU were combined with 200 µL LB+kanamycin (30 µg/mL) in each well. Wells with only media but no phage were included as untreated biofilm controls. MBEC lids with 24 h pre-grown *E. coli* biofilm were removed from their old 96-well microtiter plates, and placed into the new microtiter plates and back into plastic bags in a shaker at 35° C. and 150 rpm for treatment. After specified amounts of time for the time-course experiment or 24 h for all other experiments, MBEC lids were removed and the amounts of biofilm remaining were assayed by CV staining or viable cell counting, as described below.

Crystal violet (CV) staining assay. Crystal violet staining of MBEC pegs was carried out, after rinsing three times with 1× phosphate-buffered saline (PBS), using a standard, previously reported protocol as described in Supporting Methods (50).

Viable cell count assay. We obtained viable cell counts by disrupting biofilms on the pegs in a sonicating water bath. MBEC pegs were first rinsed three times with 200 µL of 1×PBS and placed into fresh microtiter plates (NUNC #262162) containing 145 µL of 1×PBS in each well, which completely covered the biofilms growing on the pegs. To prevent further infection of bacteria by phage, 20 ng of T7 Tail Fiber Monoclonal Antibody (NOVAGEN) was added to each well. MBEC lids and plates were placed in a Branson Ultrasonics #5510 sonic water bath (Danbury, Conn.) and sonicated for 30 minutes at 40 kHz to dislodge bacteria in biofilms into the wells. Serial dilutions were performed and plated on LB agar+kanamycin (30 µg/mL) plates. Colony-forming units were counted after overnight incubation at 37° C.

Scanning electron microscopy. SEM was performed according to MBEC recommendations (51).

Phage counts. At indicated time points (FIG. 4D) or after 24 h of treatment (FIG. 3C and FIG. 4F), media from n=3 microtiter wells for each treatment type were serially diluted to obtain PFU counts for phage in the liquid phase. To obtain PFU counts for phage residing in biofilms at 24 h post-infection (FIG. 3C), MBEC pegs were rinsed three times with 200 µL of 1× phosphate-buffered saline (PBS) and placed into fresh microtiter plates (NUNC #262162) containing 145 µL of 1×PBS in each well, which completely covered the biofilm on the pegs. No T7 Tail Fiber Monoclonal Antibody was added. The MBEC lids and plates were placed in a Branson Ultrasonics #5510 sonic water bath (Danbury, Conn.) and sonicated for 30 minutes at 40 kHz to dislodge bacteria and phage residing in biofilms into wells. Serial dilutions were performed to obtain PFU counts for phage in biofilms.

Statistical analysis. Student's unpaired two-sided t-test was used to test for statistical significance as described in Supporting Methods. For the CV staining assays, the dataset size for each treatment type was n=16; for the CFU assays, n=12 pegs per treatment type were used.

Standard chemicals. T4 DNA ligase and all restriction enzymes were obtained from New England Biolabs, Inc. (Ipswich, Mass.). PCR reactions were carried out using PCR SuperMix High Fidelity from INVITROGEN (Carlsbad, Calif.). Restriction digests of T7 genomic DNA were purified with the QIAEX II kit, while purification of all other PCR reactions and restriction digests was carried out with the QIAQUICK Gel Extraction or PCR Purification kits (QIAGEN, Valencia, Calif.). All other chemicals were purchased from Fisher Scientific, Inc. (Hampton, N.H.).

Construction and purification of engineered phage. Our engineered T7 phage was created using the T7SELECT415-1 phage display system (NOVAGEN). Instead of cloning DspB onto the phage surface, we designed the T7select phage to express DspB intracellularly during infection. The dspB gene was cloned from *Actinobacillus actinomycetemcomitans* genomic DNA (ATCC #700685D) into the pET-9a plasmid (Novagen) under the control of the strong T7 φ10 promoter in between the NdeI and BamHI sites using the forward primer 5' atataatc catatg aat tgt tgc gta aaa ggc aat tc 3' (SEQ ID NO: 1) and reverse primer 5' atatac ggatcc tca ctc atc ccc att cgt ct 3' (SEQ Id NO: 2) (restriction sites underlined). We placed a stop codon in all three reading frames downstream of the T7SELECT415-1 10B capsid gene followed by the φ10-dspB construct, so dspB would be strongly transcribed by T7 RNA polymerase during infection (FIG. 2B). The φ10-dspB construct was isolated by PCR with the primers 5' gTA AcT AA cgaaattaat acgactcact atagg 3' (SEQ ID NO: 3) and 5' atataa cggccg c aagctt tca ctc atc ccc att cgt ct 3' (SEQ ID NO: 4) (stop codons in uppercase letters); the product was used in a subsequent PCR reaction with the primers 5' tactc gaattc t TAA gTA AcT AA cgaaattaat acgactc 3'(SEQ ID NO: 5) and 5' atataa cggccg c aagctt tca ctc atc ccc att cgt ct 3' (SEQ ID NO: 6) to create a construct beginning with stop codons in each reading frame followed by the φ10-dspB construct. Both the product of this PCR reaction and the T7SELECT415-1 DNA were digested with EcoRI and EagI, purified, ligated together using T4 DNA ligase, and packaged into T7 phage particles with T7select packaging extracts to create phage T7DspB-precursor. The control phage, T7control-precursor, was constructed by cloning the T7select control S•Tag insert into the T7SELECT415-1 phage genome and packaging the genome using T7select packaging extracts (FIG. 2C). Phage T7DspB-precursor and T7control-precursor were routinely amplified on $E.$ $coli$ BL21 and verified by DNA sequencing.

Since wild-type T7 is unable to replicate normally in F-plasmid-containing $E.$ $coli$, we cloned gene 1.2 from phage T3 into T7DspB-precursor and T7control-precursor to create T7DspB and T7control, respectively, which are able to escape exclusion by the F plasmid (FIGS. 2B and 2C) (33). Genomic DNA from T7DspB-precursor and T7control-precursor was isolated using the QIAGEN Lambda Midi Kit. T3 gene 1.2 was cloned from the T3 genome using primers 5' cgta tgatca aacg agcagggcga acagtg 3' (SEQ ID NO: 7) and 5' cgta tgatca ccactc gttaaagtga ccttaaggat tc 3' (SEq ID NO: 8) and inserted into the unique BclI site in both the T7DspB-precursor and T7control-precursor, which were then packaged with T7select packaging extracts. The resulting phage were amplified on $E.$ $coli$ BL21 and then plated on $E.$ $coli$ TG1(lacI::kan) to isolate T7DspB (FIG. 2B) and T7control (FIG. 2C), which were confirmed by PCR to have gene 1.2 from T3.

Crystal violet staining assay. MBEC pegs were rinsed three times with 200 μL of 1× phosphate-buffered saline (PBS) and placed into fresh microtiter plates with wells containing 200 μL of 1% CV. After 15 minutes of incubation at room temperature, the stained MBEC pegs were washed three times with 200 μL of 1×PBS and placed into fresh microtiter plates containing 200 μL of 33% acetic acid to solubilize the dye for 15 minutes (50). To avoid oversaturating the absorbance detector, 66.7 μL of the solubilized dye was added to 133.3 μL of 1×PBS; the absorbance at 600 nm of this mixture was assayed in a TECAN SPECTRAFLUOR Plus plate reader (Zurich, Switzerland). The mean A600 nm of wells corresponding to pegs with no biofilm growth was used as a blank measurement to correct all other A600 nm absorbances.

Scanning electron microscopy. Scanning electron microscopy was carried out with a Carl Zeiss Supra 40 VP SEM using Carl Zeiss SMARTSEM V05.01.08 software. Biofilm pegs were broken off at indicated time points and washed three times in 1×PBS. The pegs were then fixed in 2.5% glutaraldehyde in 0.1 M cacodylic acid (pH 7.2) for 2 to 3 h at room temperature. Subsequently, the pegs were air dried for at least 120 h, and mounted and examined by SEM in VPSE mode with EHT=7.5 kV. Each peg was examined at several locations prior to imaging to ensure that characteristic images were acquired. Images were frame- or line-integrated using the SMARTSEM software to achieve better resolution.

Statistical analysis. Data for time-course CFU counts were collected from three independent experiments; all other CFU data were obtained from single experiments in time. Absorbance from crystal violet staining assays or CFU counts from viable cell count assays were evaluated for statistically significant differences using Student's unpaired two-sided t-test (assuming unknown and unequal variances) with an alpha level of 0.05 implemented in MATLAB version 7.0.01 (MATHWORKS, Natick, Mass.). All CFU data were log 10-transformed prior to analysis. All absorbance data and log 10-transformed CFU data were verified to be approximately normally distributed using the qqplot( ) function in MATLAB version 7.0.1 to meet the assumptions of the t-test. Error bars in figures indicate standard error of the mean (s.e.m).

REFERENCES

The references cited herein and throughout the specification and examples are herein incorporated by reference in their entirety.
1. Endy, D (2005) Nature 438: 449-453.
2. Andrianantoandro, E, Basu, S, Karig, D K & Weiss, R (2006) Mol Syst Biol 2: 2006.0028.
3. Hasty, J, McMillen, D & Collins, J J (2002) Nature 420: 224-230.
4. Tian, J, Gong, H, Sheng, N, Zhou, X, Gulari, E, Gao, X & Church, G (2004) Nature 432: 1050-1054.
5. Ro, D-K, Paradise, E M, Ouellet, M, Fisher, K J, Newman, K L, Ndungu, J M, Ho, K A, Eachus, R A, Ham, T S, Kirby, J, Chang, M C Y, Withers, S T, Shiba, Y, Sarpong, R & Keasling, J D (2006) Nature 440: 940-943.
6. Anderson, J C, Clarke, E J, Arkin, A P & Voigt, C A (2006) J Mol Biol 355: 619-627.
7. Loose, C, Jensen, K, Rigoutsos, I & Stephanopoulos, G (2006) Nature 443: 867-869.
8. Xavier, J B, Picioreanu, C, Rani, S A, van Loosdrecht, M C M & Stewart, P S (2005) Microbiology 151: 3817-3832.
9. Davey, M E & O'Toole, G A (2000) Microbiol Mol Biol Rev 64: 847-867.
10. Kolter, R & Greenberg, E P (2006) Nature 441: 300-302.
11. Parsek, M R & Singh, P K (2003) Annual Review of Microbiology 57: 677-701.
12. Costerton, J W, Lewandowski, Z, Caldwell, D E, Korber, D R & Lappin-Scott, H M (1995) Annu Rev Microbiol 49: 711-745.
13. Costerton, J W, Stewart, P S & Greenberg, E P (1999) Science 284: 1318-1322.
14. Stewart, P S & Costerton, J W (2001) Lancet 358: 135-138.
15. Hoffman, L R, D'Argenio, D A, MacCoss, M J, Zhang, Z, Jones, R A & Miller, S I (2005) Nature 436: 1171-1175.
16. Curtin, J J & Donlan, R M (2006) Antimicrob Agents Chemother 50: 1268-1275.
17. Merril, C R, Scholl, D & Adhya, S L (2003) Nat Rev Drug Discov 2: 489-497.
18. Doolittle, M M, Cooney, J J & Caldwell, D E (1995) Can J Microbiol 41: 12-18.
19. Doolittle, M M, Cooney, J J & Caldwell, D E (1996) J Ind Microbiol 16: 331-341.
20. Corbin, B D, McLean, R J & Aron, G M (2001) Can J Microbiol 47: 680-684.
21. Scholl, D, Adhya, S & Merril, C (2005) Appl Environ Microbiol 71: 4872-4874.
22. Itoh, Y, Wang, X, Hinnebusch, B J, Preston, J F & Romeo, T (2005) J Bacteriol 187: 382-387.

23. Whitchurch, C B, Tolker-Nielsen, T, Ragas, P C & Mattick, J S (2002) Science 295: 1487.
24. Hughes, K A, Sutherland, I W & Jones, M V (1998) Microbiology 144 (Pt 11): 3039-3047.
25. Hughes, K A, Sutherland, I W, Clark, J & Jones, M V (1998) Journal of Applied Microbiology 85: 583-590.
26. Projan, S (2004) Nat Biotechnol 22: 167-168.
27. Chan, L Y, Kosuri, S & Endy, D (2005) Mol Syst Biol 1: 2005.0018.
28. Itaya, M, Tsuge, K, Koizumi, M & Fujita, K (2005) Proc Natl Acad Sci USA 102: 15971-15976.
29. Dunn, J J & Studier, F W (1983) J Mol Biol 166: 477-535.
30. Studier, F W & Dunn, J J (1983) Cold Spring Harb Symp Quant Biol 47 Pt 2: 999-1007.
31. Ghigo, J M (2001) Nature 412: 442-445.
32. Re, S D, Quéré, B L, Ghigo, J-M & Beloin, C (2007) Appl Environ Microbiol.
33. Garcia, L R & Molineux, I J (1995) J Bacteriol 177: 4077-4083.
34. Studier, F W (1972) Science 176: 367-376.
35. Merril, C R, Biswas, B, Carlton, R, Jensen, N C, Creed, G J, Zullo, S & Adhya, S (1996) Proc Natl Acad Sci USA 93: 3188-3192.
36. Summers, W C (2001) Annual Review of Microbiology 55: 437-451.
37. Shuren, J (2006), ed. U.S. Food and Drug Administration, H (Federal Register, Vol. 71, pp. 47729-47732.
38. Schoolnik, G K, Summers, W C & Watson, J D (2004) Nat Biotechnol 22: 505-506; author reply 506-507.
39. Hagens, S & Blasi, U (2003) Lett Appl Microbiol 37: 318-323.
40. Hagens, S, Habel, AvAU, von Gabain, A & Blasi, U (2004) Antimicrob Agents Chemother 48: 3817-3822.
41. Boratynski, J, Syper, D, Weber-Dabrowska, B, Lusiak-Szelachowska, M, Pozniak, G & Gorski, A (2004) Cell Mol Biol Lett 9: 253-259.
42. Bartlett, J G (2006) Ann Intern Med 145: 758-764.
43. Aslam, S, Hamill, R J & Musher, D M (2005) Lancet Infect Dis 5: 549-557.
44. Baker, D, Church, G, Collins, J, Endy, D, Jacobson, J, Keasling, J, Modrich, P, Smolke, C & Weiss, R (2006) Sci Am 294: 44-51.
45. Hickman-Brenner, F W, Stubbs, A D & Farmer, J J (1991) J Clin Microbiol 29: 2817-2823.
46. Wentworth, B B (1963) Bacteriol Rev 27: 253-272.
47. Doulatov, S, Hodes, A, Dai, L, Mandhana, N, Liu, M, Deora, R, Simons, R W, Zimmerly, S & Miller, J F (2004) Nature 431: 476-481.
48. Liu, M, Deora, R, Doulatov, S R, Gingery, M, Eiserling, F A, Preston, A, Maskell, D J, Simons, R W, Cotter, P A, Parkhill, J & Miller, J F (2002) Science 295: 2091-2094.
49. Datsenko, K A & Wanner, B L (2000) Proc Natl Acad Sci USA 97: 6640-6645.
50. Jackson, D W, Suzuki, K, Oakford, L, Simecka, J W, Hart, M E & Romeo, T (2002) J Bacteriol 184: 290-301.
51. Ceri, H, Olson, M E, Stremick, C, Read, R R, Morck, D & Buret, A (1999) J Clin Microbiol 37: 1771-1776.

We claim:

1. A method of dispersing a bacterial biofilm on a surface comprising administering to said surface a genetically engineered lytic T7 bacteriophage wherein the bacteriophage comprises a nucleic acid encoding dispersin B enzyme operably linked to a strong promoter and a nucleic acid encoding a protein to enhance or expand infectivity and or replication capacity of the lytic T7 bacteriophage, wherein the nucleic acid encoding the protein to enhance or expand infectivity and or replication capacity of the lytic T7 bacteriophage encodes T3 1.2 protein.

2. The method of claim 1, wherein the strong promoter is T7 $\phi$10.

3. The method of claim 1, wherein the biofilm is a mature biofilm.

4. The method of claim 1, wherein the biofilm comprises β-1,6-N-acetyl-D-glucosamine.

5. The method of claim 4 further comprising a step of prior to administering the bacteriophage, determining if the biofilm comprises β-1,6-N-acetyl-D-glucosamine, and if it does, then administering the engineered lytic bacteriophage.

6. The method of claim 1, wherein the biofilm is formed by—*Staphylococcus* and *E. coli*, including *E. coli* K-12 strain, and clinical isolates of *E. coli*.

7. The method of claim 1, wherein the administering is performed once.

8. The method of claim 1, wherein the administering is performed before, after or concurrently with an antibiotic or antimicrobial agent.

9. The method of claim 1, wherein the administering is performed before, after or concurrently with a biofilm degrading chemical.

10. The method of claim 1, wherein the phage further comprises a terminator sequence.

* * * * *

SEQUENCE LISTING

```
<160> NUMBER OF SEQ ID NOS: 10

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atataatcca tatgaattgt tgcgtaaaag gcaattc                                  37

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atatacggat cctcactcat ccccattcgt ct                                       32

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtaactaacg aaattaatac gactcactat agg                                      33
```

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
atataacggc cgcaagcttt cactcatccc cattcgtct            39

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tactcgaatt cttaagtaac taacgaaatt aatacgactc            40

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
atataacggc cgcaagcttt cactcatccc cattcgtct            39

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
cgtatgatca aacgagcagg gcgaacagtg            30

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
cgtatgatca ccactcgtta aagtgacctt aaggattc            38

<210> SEQ ID NO 9
<211> LENGTH: 38914
<212> TYPE: DNA
<213> ORGANISM: Artificial Sequence
<220> FEATURE:
<223> OTHER INFORMATION: Description of Artificial Sequence: Synthetic construct

<400> SEQUENCE: 9
tctcacagtg tacggaccta aagttccccc atagggggta cctaaagccc agccaatcac    60
ctaaagtcaa ccttcggttg accttgaggg ttccctaagg gttggggatg acccttgggt    120
ttgtctttgg gtgttacctt gagtgtctct ctgtgtccct atctgttaca gtctcctaaa    180

```
gtatcctcct aaagtcacct cctaacgtcc atcctaaagc caacacctaa agcctacacc      240
taaagaccca tcaagtcaac gcctatctta aagtttaaac ataaagacca gacctaaaga      300
ccagacctaa agacactaca taaagaccag acctaaagac gccttgttgt tagccataaa      360
gtgataacct ttaatcattg tctttattaa tacaactcac tataaggaga gacaacttaa      420
agagacttaa aagattaatt taaaatttat caaaagagt attgacttaa agtctaacct       480
ataggatact tacagccatc gagagggaca cggcgaatag ccatcccaat cgacaccggg      540
gtcaaccgga taagtagaca gcctgataag tcgcacgaca gaaagaaatt gaccgcgcta      600
aggcccgtaa agaacgtcac gagggcgct tagaggcacg cagattcaaa cgtcgcaacc       660
gcaaggcacg taaagcacac aaagctaagc gcgaaagaat gcttgctgcg tggcgatggg      720
ctgaacgtca agaacggcgt aaccatgagg tagctgtaga tgtactagga agaaccaata     780
acgctatgct ctgggtcaac atgttctctg ggactttaa ggcgcttgag gaacgaatcg       840
cgctgcactg gcgtaatgct gaccggatgg ctatcgctaa tggtcttacg ctcaacattg     900
ataagcaact tgacgcaatg ttaatgggct gatagtctta tcttacaggt catctgcggg     960
tggcctgaat aggtacgatt tactaactgg aagaggcact aaatgaacac gattaacatc    1020
gctaagaacg acttctctga catcgaactg gctgctatcc cgttcaacac tctggctgac    1080
cattacggtg agcgtttagc tcgcaacag ttggcccttg agcatgagtc ttacgagatg     1140
ggtgaagcac gcttccgcaa gatgtttgag cgtcaactta aagctggtga ggttgcggat    1200
aacgctgccg ccaagcctct catcactacc ctactcccta agatgattgc acgcatcaac    1260
gactggtttg aggaagtgaa agctaagcgc ggcaagcgcc cgacagcctt ccagttcctg    1320
caagaaatca gccggaagc cgtagcgtac atcaccatta agaccactct ggcttgccta     1380
accagtgctg acaatacaac cgttcaggct gtagcaagcg caatcggtcg ggccattgag    1440
gacgaggctc gcttcggtcg tatccgtgac cttgaagcta agcacttcaa gaaaaacgtt    1500
gaggaacaac tcaacaagcg cgtagggcac gtctacaaga aagcatttat gcaagttgtc    1560
gaggctgaca tgctctctaa gggtctactc ggtggcgagg cgtggtcttc gtggcataag    1620
gaagactcta ttcatgtagg agtacgctgc atcgagatgc tcattgagtc aaccggaatg    1680
gttagcttac accgccaaaa tgctggcgta gtaggtcaag actctgagac tatcgaactc    1740
gcacctgaat acgctgaggc tatcgcaacc cgtgcaggtg cgctggctgg catctctccg    1800
atgttccaac cttgcgtagt tcctcctaag ccgtggactg gcattactgg tggtggctat    1860
tgggctaacg tcgtcgtcc tctggcgctg gtgcgtactc acagtaagaa agcactgatg     1920
cgctacgaag acgtttacat gcctgaggtg tacaaagcga ttaacattgc gcaaaacacc    1980
gcatggaaaa tcaacaagaa agtcctagcg gtcgccaacg taatcaccaa gtggaagcat    2040
tgtccggtcg aggacatccc tgcgattgag cgtgaagaac tcccgatgaa accggaagac    2100
atcgacatga atcctgaggc tctcaccgcg tggaaacgtg ctgccgctgc tgtgtaccgc    2160
aaggacaagg ctcgcaagtc tcgccgtatc agccttgagt tcatgcttga gcaagccaat    2220
aagtttgcta accataaggc catctggttc ccttacaaca tggactggcg cggtcgtgtt    2280
tacgctgtgt caatgttcaa cccgcaaggt aacgatatga ccaaaggact gcttacgctg    2340
gcgaaaggta aaccaatcgg taaggaaggt tactactggc tgaaaatcca cggtgcaaac    2400
tgtgcgggtg tcgataaggt tccgttccct gagcgcatca agttcattga ggaaaaccac    2460
gagaacatca tggcttgcgc taagtctcca ctggagaaca cttggtgggc tgagcaagat    2520
tctccgttct gcttccttgc gttctgcttt gagtacgctg gggtacagca ccacggcctg    2580
```

```
agctataact gctcccttcc gctggcgttt gacgggtctt gctctggcat ccagcacttc   2640
tccgcgatgc tccgagatga ggtaggtggt cgcgcggtta acttgcttcc tagtgaaacc   2700
gttcaggaca tctacgggat tgttgctaag aaagtcaacg agattctaca agcagacgca   2760
atcaatggga ccgataacga agtagttacc gtgaccgatg agaacactgg tgaaatctct   2820
gagaaagtca agctgggcac taaggcactg gctggtcaat ggctggctta cggtgttact   2880
cgcagtgtga ctaagcgttc agtcatgacg ctggcttacg ggtccaaaga gttcggcttc   2940
cgtcaacaag tgctggaaga taccattcag ccagctattg attccggcaa gggtctgatg   3000
ttcactcagc cgaatcaggc tgctggatac atggctaagc tgatttggga atctgtgagc   3060
gtgacggtgg tagctgcggt tgaagcaatg aactggctta agtctgctgc taagctgctg   3120
gctgctgagg tcaaagataa gaagactgga gagattcttc gcaagcgttg cgctgtgcat   3180
tgggtaactc ctgatggttt ccctgtgtgg caggaataca agaagcctat tcagacgcgc   3240
ttgaacctga tgttcctcgg tcagttccgc ttacagccta ccattaacac caacaaagat   3300
agcgagattg atgcacacaa acaggagtct ggtatcgctc ctaactttgt acacagccaa   3360
gacggtagcc accttcgtaa gactgtagtg tgggcacacg agaagtacgg aatcgaatct   3420
tttgcactga ttcacgactc cttcggtacc attccggctg acgctgcgaa cctgttcaaa   3480
gcagtgcgcg aaactatggt tgacacatat gagtcttgtg atgtactggc tgatttctac   3540
gaccagttcg ctgaccagtt gcacgagtct caattggaca aaatgccagc acttccggct   3600
aaaggtaact tgaacctccg tgacatctta gagtcggact tcgcgttcgc gtaacgccaa   3660
atcaatacga ctcactatag agggacaaac tcaaggtcat tcgcaagagt ggcctttatg   3720
attgacctcc ttccggttaa tacgactcac tataggagaa ccttaaggtt taacttcaag   3780
acccttaagt gttaattaga gatttaaatt aaagaattac taagagagga ctttaagtat   3840
gcgtaacttc gaaaagatga ccaaacgttc taaccgtaat gctcgtgact tcgaggcaac   3900
caaaggtcgc aagttgaata agactaagcg tgaccgctct cacaagcgta gctgggaggg   3960
tcagtaagat gggacgttta tatagtggta atctggcagc attcaaggca gcaacaaaca   4020
agctgttcca gttagactta gcggtcattt atgatgactg gtatgatgcc tatacaagaa   4080
aagattgcat acggttacgt attgaggaca ggagtggaaa cctgattgat actagcacct   4140
tctaccacca cgacgaggac gttctgttca atatgtgtac tgattggttg aaccatatgt   4200
atgaccagtt gaaggactgg aagtaatacg actcagtata gggacaatgc ttaaggtcgc   4260
tctctaggag tggccttagt catttaacca ataggagata acattatga tgaacattaa   4320 gactaacccg tttaaagccg tgtctttcgt agagtctgcc attaagaagg ctctggataa   4380
cgctgggtat cttatcgctg aaatcaagta cgatggtgta cgcgggaaca tctgcgtaga   4440
caatactgct aacagttact ggctctctcg tgtatctaaa acgattccgg cactggagca   4500
cttaaacggg tttgatgttc gctggaagcg tctactgaac gatgaccgtt gcttctacaa   4560
agatggcttt atgcttgatg gggaactcat ggtcaagggc gtagactta acacagggtc   4620 cggcctactg cgtaccaaat ggactgacac gaagaaccaa gagttccatg aagagttatt   4680
cgttgaacca atccgtaaga agataaagt tccctttaag ctgcacactg acaccttca   4740 cataaaactg tacgctatcc tcccgctgca catcgtggag tctggagaag actgtgatgt   4800
catgacgttg ctcatgcagg aacacgttaa gaacatgctg cctctgctac aggaatactt   4860 cccctgaaatc gaatggcaag cggctgaatc ttacgaggtc tacgatatgg tagaactaca   4920
gcaactgtac gagcagaagc gagcagaagg ccatgagggt ctcattgtga aagacccgat   4980
```

```
gtgtatctat aagcgcggta agaaatctgg ctggtggaaa atgaaacctg agaacgaagc    5040
tgacggtatc attcagggtc tggtatgggg tacaaaaggt ctggctaatg aaggtaaagt    5100
gattggtttt gaggtgcttc ttgagagtgg tcgtttagtt aacgccacga atatctctcg    5160
cgccttaatg gatgagttca ctgagacagt aaaagaggcc accctaagtc aatggggatt    5220
ctttagccca tacggtattg gcgacaacga tgcttgtact attaacccct acgatggctg    5280
ggcgtgtcaa attagctaca tggaggaaac acctgatggc tctttgcggc acccatcgtt    5340
cgtaatgttc cgtggcaccg aggacaaccc tcaagagaaa atgtaatcac actggctcac    5400
cttcgggtgg gccttctctgc gtttataagg agacacttta tgtttaagaa ggttggtaaa    5460
ttccttgcgg cttttggcagc tatcctgacg cttgcgtata ttcttgcggt atacccctcaa    5520 gtagcactag tagtagttgg cgcttgttac ttagcggcag tgtgtgcttg cgtgtggagt    5580
atagttaact ggtaatacga ctcactaaag gaggtacaca ccatgatgta cttaatgcca    5640
ttactcatcg tcattgtagg atgccttgcg ctccactgta gcgatgatga tatgccagat    5700
ggtcacgctt aatacgactc actaaaggag acactatatg tttcgacttc attacaacaa    5760
aagcgttaag aatttcacgg ttcgccgtgc tgaccgttca atcgtatgtg cgagcgagcg    5820
ccgagctaag atacctctta ttggtaacac agttcctttg gcaccgagcg tccacatcat    5880
tatcacccgt ggtgactttg agaaagcaat agacaagaaa cgtccggttc ttagtgtggc    5940
agtgacccgc ttcccgttcg tccgtctgtt actcaaacga atcaaggagg tgttctgatg    6000
ggactgttag atggtgaagc ctgggaaaaa gaaaacccgc cagtacaagc aactgggtgt    6060
atagcttgct tagagaaaga tgaccgttat ccacacacct gtaacaaagg agctaacgat    6120
atgaccgaac gtgaacaaga gatgatcaaa cgagcagggc gaacagtggc aagagcgccg    6180
tgaccgcatg aagaaacgcc acaagcaaca gcgcggtaac tcacagaaac gggagtggaa    6240
ctgatgatga tgggacgtat ttatagcggc aacctgaacg attacaaaga tgcggtagcg    6300
cgtctacagg aagaccatga tgtgaccgtg aagatggagt cattcagcta cgaaaaccca    6360
gcgaagatgt gcaggtcatg cggtgaggtt ctcagtgtgt tcacacgctc cgggcatctg    6420
gtggcatcca gaaccttcga gcatagcgac agcgatgtac aaatcaacgc gcagactgca    6480
tggctccgta aggttcacag cgaattgaaa cactggaagt aataaccctc actaacagga    6540
gaatccttaa ggtcacttta acgagtggtg atcattaagt tgatagacaa taatgaaggt    6600
cgcccagatg atttgaatgg ctgcggtatt ctctgctcca atgtcccttg ccacctctgc    6660
cccgcaaata acgatcaaaa gataaacctta ggtgaaatcc gagcgatgga cccacgtaaa    6720
ccacatctga ataaacctga ggtaactcct acagatgacc agccttccgc tgagacaatc    6780
gaaggtgtca ctaagccttc ccactacatg ctgtttgacg acattgaggc tatcgaagtg    6840
attgctcgtt caatgaccgt tgagcagttc aagggatact gcttcggtaa catcttaaag    6900
tacagactac gtgctggtaa gaagtcagag ttagcgtact tagagaaaga cctagcgaaa    6960
gcagacttct ataaagaact cttttgagaaa cataaggata aatgttatgc ataacttcaa    7020 gtcaaccccca cctgccgaca gcctatctga tgacttcaca tcttgctcag agtggtgccg    7080
aaagatgtgg gaagagacat tcgacgatgc gtacatcaag ctgtatgaac tttggaaatc    7140
gagaggtcaa tgactatgtc aaacgtaaat acaggttcac ttagtgtgga caataagaag    7200
ttttgggcta ccgtagagtc ctcggagcat tccttcgagg ttccaatcta cgctgagacc    7260
ctagacgaag ctctggagtt agccgaatgg caatacgttc cggctggctt tgaggttact    7320
cgtgtgcgtc cttgtgtagc accgaagtaa tacgactcac tattagggaa gactccctct    7380
```

```
gagaaaccaa acgaaaccta aaggagatta acattatggc taagaagatt ttcacctctg   7440
cgctgggtac cgctgaacct tacgcttaca tcgccaagcc ggactacggc aacgaagagc   7500
gtggctttgg gaaccctcgt ggtgtctata agttgacct  gactattccc aacaaagacc   7560
cgcgctgcca gcgtatggtc gatgaaatcg tgaagtgtca cgaagaggct tatgctgctg   7620
ccgttgagga atacgaagct aatccacctg ctgtagctcg tggtaagaaa ccgctgaaac   7680
cgtatgaggg tgacatgccg ttcttcgata acggtgacgg tacgactacc tttaagttca   7740
aatgctacgc gtcttttccaa gacaagaaga ccaaagagac caagcacatc aatctggttg   7800
tggttgactc aaaaggtaag aagatggaag acgttccgat tatcggtggt ggctctaagc   7860
tgaaagttaa atattctctg gttccataca agtggaacac tgctgtaggt gcgagcgtta   7920
agctgcaact ggaatccgtg atgctggtcg aactggctac ctttggtggc ggtgaagacg   7980
attgggctga cgaagttgaa gagaacggct atgttgcctc tggttctgcc aaagcgagca   8040
aaccacgcga cgaagaaagc tgggacgaag acgacgaaga gtccgaggaa gcagacgaag   8100
acggagactt ctaagtggaa ctgcgggaga aaatccttga gcgaatcaag gtgacttcct   8160
ctgggtgttg ggagtggcag ggcgctacga acaataaagg gtacgggcag gtgtggtgca   8220
gcaataccgg aaaggttgtc tactgtcatc gcgtaatgtc taatgctccg aaaggttcta   8280
ccgtcctgca ctcctgtgat aatccattat gttgtaaccc tgaacaccta tccataggaa   8340
ctccaaaaga gaactccact gacatggtaa ataagggtcg ctcacacaag gggtataaac   8400
tttcagacga gacgtaatg  gcaatcatgg agtccagcga gtccaatgta tccttagctc   8460
gcacctatgg tgtctcccaa cagactatt  gtgatatacg caaagggagg cgacatggca   8520
ggttacggcg ctaaaggaat ccgaaaggtt ggagcgtttc gctctggcct agaggacaag   8580
gtttcaaagc agttggaatc aaaaggtatt aaattcgagt atgaagagtg gaaagtgcct   8640
tatgtaattc cggcgagcaa tcacacttac actccagact tcttacttcc aaacggtata   8700
ttcgttgaga caaagggtct gtgggaaagc gatgatagaa agaagcactt attaattagg   8760
gagcagcacc ccgagctaga catccgtatt gtcttctcaa gctcacgtac taagttatac   8820
aaaggttctc caacgtctta tggagagttc tgcgaaaagc atggtattaa gttcgctgat   8880
aaactgatac ctgctgagtg gataaaggaa cccaagaagg aggtcccctt tgatagatta   8940
aaaaggaaag gaggaaagaa ataatggctc gtgtacagtt taaacaacgt gaatctactg   9000
acgcaatctt tgttcactgc tcggctacca agccaagtca gaatgttggt gtccgtgaga   9060
ttcgccagtg gcacaaagag cagggttggc tcgatgtggg ataccacttt atcatcaagc   9120
gagacggtac tgtggaggca ggacgagatg agatggctgt aggctctcac gctaagggtt   9180
acaaccacaa ctctatcggc gtctgccttg ttggtggtat cgacgataaa ggtaagttcg   9240
acgctaactt tacgccagcc caaatgcaat cccttcgctc actgcttgtc acactgctgg   9300
ctaagtacga aggcgctggt cttcgcgccc atcatgaggt ggcgccgaag gcttgccctt   9360
cgttcgacct taagcgttgg tgggagaaga acgaactggt cacttctgac cgtggataat   9420
gatctattgg aagtcgttgc gtggatttat agaactagga gggaattgca tggacaattc   9480
gcacgattcc gatagtgtat ttctttacca cattccttgt gacaactgtg ggagtagtga   9540
tgggaactcg ctgttctctg acggacacac gttctgctac gtatgcgaga agtggactgc   9600
tggtaatgaa gacactaaag agagggcttc aaaacggaaa ccctcaggag gtaaaccaat   9660
gacttacaac gtgtggaact tcggggaatc caatggacgc tactccgcgt taactgcgag   9720
aggaatctcc aaggaaacct gtcagaaggc tggctactgg attgccaaag tagacggtgt   9780
```

```
gatgtaccaa gtggctgact atcgggacca gaacggcaac attgtgagtc agaaggttcg   9840
agataaagat aagaacttta agaccactgg tagtcacaag agtgacgctc tgttcgggaa   9900
gcacttgtgg aatggtggta agaagattgt cgttacagaa ggtgaaatcg acatgcttac   9960
cgtgatggaa cttcaagact gtaagtatcc tgtagtgtcg ttgggtcacg gtgcctctgc  10020
cgctaagaag acatgcgctg ccaactacga atactttgac cagttcgaac agattatctt  10080
aatgttcgat atggacgaag cagggcgcaa agcagtcgaa gaggctgcac aggttctacc  10140
tgctggtaag gtacgagtgg cagttcttcc gtgtaaggat gcaaacgagt gtcacctaaa  10200
tggtcacgac cgtgaaatca tggagcaagt gtggaatgct ggtccttgga ttcctgatgg  10260
tgtggtatcg gctctttcgt tacgtgaacg aatccgtgag cacctatcgt ccgaggaatc  10320
agtaggttta cttttcagtg gctgcactgg tatcaacgat aagaccttag gtgcccgtgg  10380
tggtgaagtc attatggtca cttccggttc cggtatgggt aagtcaacgt tcgtccgtca  10440
acaagctcta caatgggtca cagcgatggg caagaaggta ggcttagcga tgcttgagga  10500
gtccgttgag gagaccgctg aggaccttat aggtctacac aaccgtgtcc gactgagaca  10560
atccgactca ctaaagagag agattattga gaacggtaag ttcgaccaat ggttcgatga  10620
actgttcggc aacgatacgt tccatctata tgactcattc gccgaggctg agacggatag  10680
actgctcgct aagctggcct acatgcgctc aggcttgggc tgtgacgtaa tcattctaga  10740
ccacatctca atcgtcgtat ccgcttctgg tgaatccgat gagcgtaaga tgattgacaa  10800
cctgatgacc aagctcaaag ggttcgctaa gtcaactggg gtggtgctgg tcgtaatttg  10860
tcaccttaag aacccagaca aggtaaagc acatgaggaa ggtcgccccg tttctattac  10920
tgacctacgt ggttctggcg cactacgcca actatctgat actattattg cccttgagcg  10980
taatcagcaa ggcgatatgc ctaaccttgt cctcgttcgt attctcaagt gccgctttac  11040
tggtgatact ggtatcgctg gctacatgga atacaacaag gaaaccggat ggcttgaacc  11100
atcaagttac tcaggggaag aagagtcaca ctcagagtca acagactggt ccaacgacac  11160
tgacttctga caggattctt gatgactttc cagacgacta cgagaagttt cgctggagag  11220
tcccattcta atacgactca ctaaaggaga cacaccatgt tcaaactgat taagaagtta  11280
ggccaactgc tggttcgtat gtacaacgtg gaagccaagc gactgaacga tgaggctcgt  11340
aaagaggcca cacagtcacg cgctctggcg attcgctcca acgaactggc tgacagtgca  11400
tccactaaag ttaccgaggc tgcccgtgtg gcaaaccaag ctcaacagct ttccaaattc  11460
tttgagtaat caaacaggag aaaccattat gtctaacgta gctgaaacta ccgtctatc  11520
cgatacagct gaccagtgga accgtcgagt ccacatcaac gttcgcaacg gtaaggcgac  11580
tatggtttac cgctggaagg actctaagtc ctctaagaat cacactcagc gtatgacgtt  11640
gacagatgag caagcactgc gtctggtcaa tgcgcttacc aaagctgccg tgacagcaat  11700
tcatgaagct ggtcgcgtca atgaagctat ggctatcctc gacaagattg ataactaaga  11760
gtggtatcct caaggtcgcc aaagtggtgg ccttcatgaa tactattcga ctcactatag  11820
gagatattac catgcgtgac cctaaagtta tccaagcaga aatcgctaaa ctggaagctg  11880
aactggagga cgttaagtac catgaagcta agactcgctc cgctgttcac atcttgaaga  11940
acttaggctg gacttggaca agacagactg gctggaagaa accagaagtt accaagctga  12000
gtcataaggt gttcgataag gacactatga cccacatcaa ggctggtgat tgggttaagg  12060
ttgacatggg agttgttggt ggatacggct acgtccgctc agttagtggc aaatatgcac  12120
aagtgtcata catcacaggt gttactccac gcggtgcaat cgttgccgat aagaccaaca  12180
```

```
tgattcacac aggtttcttg acagttgttt catatgaaga gattgttaag tcacgataat    12240
caataggaga aatcaatatg atcgtttctg acatcgaagc taacgccctc ttagagagcg    12300
tcactaagtt ccactgcggg gttatctacg actactccac cgctgagtac gtaagctacc    12360
gtccgagtga cttcggtgcg tatctggatg cgctggaagc cgaggttgca cgaggcggtc    12420
ttattgtgtt ccacaacggt cacaagtatg acgttcctgc attgaccaaa ctggcaaagt    12480
tgcaattgaa ccgagagttc caccttcctc gtgagaactg tattgacacc cttgtgttgt    12540
cacgtttgat tcattccaac ctcaaggaca ccgatatggg tcttctgcgt tccggcaagt    12600
tgcccggaaa acgctttggg tctcacgctt tggaggcgtg gggttatcgc ttaggcgaga    12660
tgaagggtga atacaaagac gactttaagc gtatgcttga agagcagggt gaagaatacg    12720
ttgacggaat ggagtggtgg aacttcaacg aagagatgat ggactataac gttcaggacg    12780
ttgtggtaac taaagctctc cttgagaagc tactctctga caaacattac ttccctcctg    12840
agattgactt tacggacgta ggatacacta cgttctggtc agaatccctt gaggccgttg    12900
acattgaaca tcgtgctgca tggctgctcg ctaaacaaga gcgcaacggg ttcccgtttg    12960
acacaaaagc aatcgaagag ttgtacgtag agttagctgc tcgccgctct gagttgctcc    13020
gtaaattgac cgaaacgttc ggctcgtggt atcagcctaa aggtggcact gagatgttct    13080
gccatccgcg aacaggtaag ccactaccta aatacgctcg cattaagaca cctaaagttg    13140
gtggtatctt taagaagcct aagaacaagg cacagcgaga aggccgtgag ccttgcgaac    13200
ttgatacccg cgagtacgtt gctggtgctc cttacacccc agttgaacat gttgtgttta    13260
acccttcgtc tcgtgaccac attcagaaga aactccaaga ggctgggtgg gtcccgacca    13320
agtacaccga taagggtgct cctgtggtgg acgatgaggt actcgaagga gtacgtgtag    13380
atgaccctga gaagcaagcc gctatcgacc tcattaaaga gtacttgatg attcagaagc    13440
gaatcggaca gtctgctgag ggagacaaag catggcttcg ttatgttgct gaggatggta    13500
agattcatgg ttctgttaac cctaatggag cagttacggg tcgtgcgacc catgcgttcc    13560
caaaccttgc gcaaattccg ggtgtacgtt ctccttatgg agagcagtgt cgcgctgctt    13620
ttggcgctga gcaccatttg gatgggataa ctggtaagcc ttgggttcag gctggcatcg    13680
acgcatccgg tcttgagcta cgctgcttgg ctcacttcat ggctcgcttt gataacggcg    13740
agtacgctca cgagattctt aacggcgaca tccacactaa gaaccagata gctgctgaac    13800
tacctacccg agataacgct aagacgttca tctatgggtt cctctatggt gctggtgatg    13860
agaagattgg acagattgtt ggtgctggta aagagcgcgg taaggaactc aagaagaaat    13920
tccttgagaa cacccccgcg attgcagcac tccgcgagtc tatccaacag acacttgtcg    13980
agtcctctca atgggtagct ggtgagcaac aagtcaagtg gaaacgccgc tggattaaag    14040
gtctggatgg tcgtaaggta cacgttcgta gtcctcacgc tgccttgaat accctactgc    14100
aatctgctgt tgctctcatc tgcaaactgt ggattatcaa gaccgaagag atgctcgtag    14160
agaaaggctt gaagcatggc tgggatgggg actttgcgta catggcatgg gtacatgatg    14220
aaatccaagt aggctgccgt accgaagaga ttgctcaggt ggtcattgag accgcacaag    14280
aagcgatgcg ctgggttgga gaccactgga acttccggtg tcttctggat accgaaggta    14340
agatgggtcc taattgggcg atttgccact gatacaggag gctactcatg aacgaaagac    14400
acttaacagg tgctgcttct gaaatgctag tagcctacaa atttaccaaa gctgggtaca    14460
ctgtctatta ccctatgctg actcagagta aagaggactt ggttgtatgt aaggatggta    14520
aatttagtaa ggttcaggtt aaaacagcca caacggttca aaccaacaca ggagatgcca    14580
```

```
agcaggttag gctaggtgga tgcggtaggt ccgaatataa ggatggagac tttgacattc   14640
ttgcggttgt ggttgacgaa gatgtgctta ttttcacatg ggacgaagta aaaggtaaga   14700
catccatgtg tgtcggcaag agaaacaaag gcataaaact ataggagaaa ttattatggc   14760
tatgacaaag aaatttaaag tgtccttcga cgttaccgca aagatgtcgt ctgacgttca   14820
ggcaatctta gagaaagata tgctgcatct atgtaagcag gtcggctcag gtgcgattgt   14880
ccccaatggt aaacagaagg aaatgattgt ccagttcctg acacacggta tggaaggatt   14940
gatgacattc gtagtacgta catcatttcg tgaggccatt aaggacatgc acgaagagta   15000
tgcagataag gactctttca aacaatctcc tgcaacagta cgggaggtgt tctgatgtct   15060
gactacctga aagtgctgca agcaatcaaa agttgcccta agactttcca gtccaactat   15120
gtacggaaca atgcgagcct cgtagcggag gccgcttccc gtggtcacat ctcgtgcctg   15180
actactagtg gacgtaacgg tggcgcttgg gaaatcactg cttccggtac tcgctttctg   15240
aaacgaatgg gaggatgtgt ctaatgtctc gtgaccttgt gactattcca cgcgatgtgt   15300
ggaacgatat acagggctac atcgactctc tggaacgtga aacgatagc cttaagaatc   15360 aactaatgga agctgacgaa tacgtagcgg aactagagga gaaacttaat ggcacttctt   15420
gaccttaaac aattctatga gttacgtgaa ggctgcgacg acaagggtat ccttgtgatg   15480
gacggcgact ggctggtctt ccaagctatg agtgctgctg agtttgatgc ctcttgggag   15540
gaagagattt ggcaccgatg ctgtgaccac gctaaggccc gtcagattct tgaggattcc   15600
attaagtcct acgagacccg taagaaggct tgggcaggtg ctccaattgt ccttgcgttc   15660
accgatagtg ttaactggcg taaagaactg gttgacccga actataaggc taaccgtaag   15720
gccgtgaaga aacctgtagg gtactttgag ttccttgatg ctctctttga gcgcgaagag   15780
ttctattgca tccgtgagcc tatgcttgag ggtgatgacg ttatgggagt tattgcttcc   15840
aatccgtctg ccttcggtgc tcgtaaggct gtaatcatct cttgcgataa ggactttaag   15900
accatcccta actgtgactt cctgtggtgt accactggta acatcctgac tcagaccgaa   15960
gagtccgctg actggtggca cctcttccag accatcaagg gtgacatcac tgatggttac   16020
tcagggattg ctggatgggg tgataccgcc gaggacttct tgaataaccc gttcataacc   16080
gagcctaaaa cgtctgtgct taagtccggt aagaacaaag gccaagaggt tactaaatgg   16140
gttaaacgcg accctgagcc tcatgagacg ctttgggact gcattaagtc cattggcgcg   16200
aaggctggta tgaccgaaga ggatattatc aagcagggcc aaatggctcg aatcctacgg   16260
ttcaacgagt acaactttat tgacaaggag atttacctgt ggagaccgta gcgtatattg   16320
gtctgggtct ttgtgttctc ggagtgtgcc tcatttcgtg gggcctttgg gacttagcca   16380
gaataatcaa gtcgttacac gacactaagt gataaactca aggtccctaa attaatacga   16440
ctcactatag ggagataggg gcctttacga ttattacttt aagatttaac tctaagagga   16500
atctttatta tgttaacacc tattaaccaa ttacttaaga accctaacga tattccagat   16560
gtacctcgtg caaccgctga gtatctacag gttcgattca actatgcgta cctcgaagcg   16620
tctggtcata taggacttat gcgtgctaat ggttgtagtg aggcccacat cttgggtttc   16680
attcagggcc tacagtatgc ctctaacgtc attgacgaga ttgagttacg caaggaacaa   16740
ctaagagatg atggggagga ttgacactat gtgtttctca ccgaaaatta aaactccgaa   16800
gatggatacc aatcagattc gagccgttga gccagcgcct ctgacccaag aagtgtcaag   16860
cgtggagttc ggtgggtctt ctgatgagac ggataccgag gcaccgaag tgtctggacg   16920 caaaggcctc aaggtcgaac gtgatgattc cgtagcgaag tctaaagcca gcggcaatgg   16980
```

```
ctccgctcgt atgaaatctt ccatccgtaa gtccgcattt ggaggtaaga agtgatgtct    17040
gagttcacat gtgtggaggc taagagtcgc ttccgtgcaa tccggtggac tgtggaacac    17100
cttgggttgc ctaaaggatt cgaaggacac tttgtgggct acagcctcta cgtagacgaa    17160
gtgatggaca tgtctggttg ccgtgaagag tacattctgg actctaccgg aaaacatgta    17220
gcgtacttcg cgtggtgcgt aagctgtgac attcaccaca aaggagacat tctggatgta    17280
acgtccgttg tcattaatcc tgaggcagac tctaagggct acagcgatt cctagcgaaa     17340
cgctttaagt accttgcgga actccacgat gcgattggg tgtctcgttg taagcatgaa      17400
ggcgagacaa tgcgtgtata ctttaaggag gtataagtta tgggtaagaa agttaagaag    17460
gccgtgaaga aagtcaccaa gtccgttaag aaagtcgtta aggaaggggc tcgtccggtt    17520
aaacaggttg ctggcggtct agctggtctg gctggtggta ctggtgaagc acagatggtg    17580
gaagtaccac aagctgccgc acagattgtt gacgtacctg agaaagaggt ttccactgag    17640
gacgaagcac agacagaaag cggacgcaag aaagctcgtg ctggcggtaa gaaatccttg    17700
agtgtagccc gtagctccgg tggcggtatc aacatttaat caggaggtta tcgtggaaga    17760
ctgcattgaa tggaccggag gtgtcaactc taagggttat ggtcgtaagt gggttaatgg    17820
taaacttgtg actccacata ggcacatcta tgaggagaca tatggtccag ttccaacagg    17880
aattgtggtg atgcatatct gcgataaccc taggtgctat aacataaagc accttacgct    17940
tggaactcca aaggataatt ccgaggacat ggttaccaaa ggtagacagg ctaaaggaga    18000
ggaactaagc aagaaactta cagagtcaga cgttctcgct atacgctctt caaccttaag    18060
ccaccgctcc ttaggagaac tgtatggagt cagtcaatca accataacgc gaatactaca    18120
gcgtaagaca tggagacaca tttaatggct gagaaacgaa caggacttgc ggaggatggc    18180
gcaaagtctg tctatgagcg tttaaagaac gaccgtgctc cctatgagac acgcgctcag    18240
aattgcgctc aatataccat cccatcattg ttccctaagg actccgataa cgcctctaca    18300
gattatcaaa ctccgtggca agccgtgggc gctcgtggtc tgaacaatct agcctctaag    18360
ctcatgctgg ctctattccc tatgcagact tggatgcgac ttactatatc tgaatatgaa    18420
gcaaagcagt tactgagcga ccccgatgga ctcgctaagg tcgatgaggg cctctcgatg    18480
gtagagcgta tcatcatgaa ctacattgag tctaacagtt accgcgtgac tctctttgag    18540
gctctcaaac agttagtcgt agctggtaac gtcctgctgt acctaccgga accggaaggg    18600
tcaaactata atcccatgaa gctgtaccga ttgtcttctt atgtggtcca acgagacgca    18660
ttcggcaacg ttctgcaaat ggtgactcgt gaccagatag cttttggtgc ctctccctgag   18720
gacatccgta aggctgtaga aggtcaaggt ggtgagaaga agctgatga gacaatcgac      18780
gtgtacactc acatctatct ggatgaggac tcaggtgaat acctccgata cgaagaggtc    18840
gagggtatgg aagtccaagg ctccgatggg acttatccta agaggcttg cccatacatc     18900
ccgattcgga tggtcagact agatggtgaa tcctacggtc gttcgtacat tgaggaatac    18960
ttaggtgact acggtcccct tgaaaatctc caagaggcta tcgtcaagat gtccatgatt    19020
agctctaagg ttatcggctt agtgaatcct gctggtatca cccagccacg ccgactgacc    19080
aaagctcaga ctggtgactt cgttactggt cgtccagaag acatctcgtt cctccaactg    19140
gagaagcaag cagactttac tgtagctaaa gccgtaagtg acgctatcga ggctcgcctt    19200
tcgtttgcct ttatgttgaa ctctgcggtt cagcgtacag gtgaacgtgt gaccgccgaa    19260
gagattcggt atgtagcttc tgaacttgaa gatactttag gtggtgtcta ctctatcctt    19320
tctcaagaat tacaattgcc tctggtacga gtgctcttga agcaactaca agccacgcaa    19380
```

```
cagattcctg agttacctaa ggaagccgta gagccaacca ttagtacagg tctggaagca   19440
attggtcgag gacaagacct tgataagctg gagcggtgtg tcactgcgtg ggctgcactg   19500
gcacctatgc gggacgaccc tgatattaac cttgcgatga ttaagttacg tattgccaac   19560
gctatcggta ttgacacttc tggtattcta ctcaccgaag aacagaagca acagaagatg   19620
gcccaacagt ctatgcaaat gggtatggat aatggtgctg ctgcgctggc tcaaggtatg   19680
gctgcacaag ctacagcttc acctgaggct atggctgctg ccgctgattc cgtaggttta   19740
cagccgggaa tttaatacga ctcactatag ggagacctca tctttgaaat gagcgatgac   19800
aagaggttgg agtcctcggt cttcctgtag ttcaacttta aggagacaat aataatggct   19860
gaatctaatg cagacgtata tgcatctttt ggcgtgaact ccgctgtgat gtctggtggt   19920
tccgttgagg aacatgagca gaacatgctg gctcttgatg ttgctgcccg tgatggcgat   19980
gatgcaatcg agttagcgtc agacgaagtg gaaacagaac gtgacctgta tgacaactct   20040
gacccgttcg gtcaagagga tgacgaaggc cgcattcagg ttcgtatcgg tgatggctct   20100
gagccgaccg atgtggacac tggagaagaa ggcgttgagg gcaccgaagg ttccgaagag   20160
tttaccccac tgggcgagac tccagaagaa ctggtagctg cctctgagca acttggtgag   20220
cacgaagagg gcttccaaga gatgattaac attgctgctg agcgtggcat gagtgtcgag   20280
accattgagg ctatccagcg tgagtacgag gagaacgaag agttgtccgc cgagtcctac   20340
gctaagctgg ctgaaattgg ctacacgaag gctttcattg actcgtatat ccgtggtcaa   20400
gaagctctgg tggagcagta cgtaaacagt gtcattgagt acgctggtgg tcgtgaacgt   20460
tttgatgcac tgtataacca ccttgagacg cacaaccctg aggctgcaca gtcgctggat   20520
aatgcgttga ccaatcgtga cttagcgacc gttaaggcta tcatcaactt ggctggtgag   20580
tctcgcgcta aggcgttcgg tcgtaagcca actcgtagtg tgactaatcg tgctattccg   20640
gctaaacctc aggctaccaa gcgtgaaggc tttgcggacc gtagcgagat gattaaagct   20700
atgagtgacc ctcggtatcg cacagatgcc aactatcgtc gtcaagtcga acagaaagta   20760
atcgattcga acttctgata gacttcgaaa ttaatacgac tcactatagg gagaccacaa   20820
cggtttccct ctagaaataa ttttgtttaa ctttaagaag gagatataca tatggctagc   20880
atgactggtg gacagcaaat gggtactaac caaggtaaag gtgtagttgc tgctggagat   20940
aaactggcgt tgttcttgaa ggtatttggc ggtgaagtcc tgactgcgtt cgctcgtacc   21000
tccgtgacca cttctcgcca catggtacgt tccatctcca gcggtaaatc cgctcagttc   21060
cctgttctgg gtcgcactca ggcagcgtat ctggctccgg gcgagaacct cgacgataaa   21120
cgtaaggaca tcaaacacac cgagaaggta atcaccattg acggtctcct gacggctgac   21180
gttctgattt atgatattga ggacgcgatg aaccactacg acgttcgctc tgagtatacc   21240
tctcagttgg gtgaatctct ggcgatggct gcggatggtg cggttctggc tgagattgcc   21300
ggtctgtgta acgtggaaag caaatataat gagaacatcg agggcttagg tactgctacc   21360
gtaattgaga ccactcagaa caaggccgca cttaccgacc aagttgcgct gggtaaggag   21420
attattgcgg ctctgactaa ggctcgtgcg gctctgacca agaactatgt tccggctgct   21480
gaccgtgtgt tctactgtga cccagatagc tactctgcga ttctggcagc actgatgccg   21540
aacgcagcaa actacgctgc tctgattgac cctgagaagg gttctatccg caacgttatg   21600
ggctttgagg ttgtagaagt tccgcacctc accgctggtg gtgctggtac cgctcgtgag   21660
ggcactactg gtcagaagca cgtcttccct gccaataaag gtgagggtaa tgtcaaggtt   21720
gctaaggaca acgttatcgg cctgttcatg caccgctctg cggtaggtac tgttaagctg   21780
```

```
cgtgacttgg ctctggagcg cgctcgccgt gctaacttcc aagcggacca gattatcgct   21840
aagtacgcaa tgggccacgg tggtcttcgc ccagaagctg caggagctgt cgtattccag   21900
tcaggtgtga tgctcgggga tccgaattct taagtaacta acgaaattaa tacgactcac   21960
tatagggaga ccacaacggt ttccctctag aaataatttt gtttaacttt aagaaggaga   22020
tatacatatg aattgttgcg taaaaggcaa ttccatatat ccgcaaaaaa caagtaccaa   22080
gcagaccgga ttaatgctgg acatcgcccg acatttttat tcacccgagg tgattaaatc   22140
ctttattgat accatcagcc tttccggcgg taattttctg cacctgcatt tttccgacca   22200
tgaaaactat gcgatagaaa gccatttact taatcaacgt gcggaaaatg ccgtgcaggg   22260
caaagacggt atttatatta atccttatac cggaaagcca ttcttgagtt atcggcaact   22320
tgacgatatc aaagcctatg ctaaggcaaa aggcattgag ttgattcccg aacttgacag   22380
cccgaatcac atgacggcga tctttaaact ggtgcaaaaa gacagagggg tcaagtacct   22440
tcaaggatta aaatcacgcc aggtagatga tgaaattgat attactaatg ctgacagtat   22500 tactttatg caatctttaa tgagtgaggt tattgatatt tttggcgaca cgagtcagca   22560
ttttcatatt ggtggcgatg aatttggtta ttctgtggaa agtaatcatg agttattac   22620 gtatgccaat aaactatcct acttttttaga gaaaaaggg ttgaaaaccc gaatgtggaa   22680
tgacggatta ttaaaaata cttttgagca aatcaacccg aatattgaaa ttacttattg   22740
gagctatgat ggcgatacgc aggacaaaaa tgaagctgcc gagcgccgtg atatgcgggt   22800
cagtttgccg gagttgctgg cgaaaggctt tactgtcctg aactataatt cctattatct   22860
ttacattgtt ccgaaagctt caccaacctt ctcgcaagat gccgcctttg ccgccaaaga   22920
tgttataaaa aattgggatc ttggtgtttg ggatggacga acaccaaaa accgcgtaca   22980 aaatactcat gaaatagccg gcgcagcatt atcgatctgg ggagaagatg caaaagcgct   23040
gaaagacgaa acaattcaga aaaacacgaa aagtttattg gaagcggtga ttcataagac   23100
gaatggggat gagtgaaagc ttgcggccgc actcgagtaa ctagttaacc ccttgggggcc   23160 tctaaacggg tcttgagggg ttttttgctg aaaggaggaa ctatatgcgc tcatacgata   23220
tgaacgttga gactgccgct gagttatcag ctgtgaacga cattctggcg tctatcggtg   23280
aacctccggt atcaacgctg gaaggtgacg ctaacgcaga tgcagcgaac gctcggcgta   23340
ttctcaacaa gattaaccga cagattcaat ctcgtggatg gacgttcaac attgaggaag   23400
gcataacgct actacctgat gtttactcca acctgattgt atacagtgac gactatttat   23460
ccctaatgtc tacttccggt caatccatct acgttaaccg aggtggctat gtgtatgacc   23520
gaacgagtca atcagaccgc tttgactctg gtattactgt gaacattatt cgtctccgcg   23580
actacgatga gatgcctgag tgcttccgtt actggattgt caccaaggct tcccgtcagt   23640
tcaacaaccg attctttggg gcaccggaag tagagggtgt actccaagaa gaggaagatg   23700
aggctagacg tctctgcatg gagtatgaga tggactacgg tgggtacaat atgctggatg   23760
gagatgcgtt cacttctggt ctactgactc gctaacatta ataaataagg aggctctaat   23820
ggcactcatt agccaatcaa tcaagaactt gaagggtggg atcagccaac agcctgacat   23880
ccttcgttat ccagaccaag ggtcacgcca agttaacggt tggtcttcgg agaccgaggg   23940
cctccaaaag cgtccacctc ttgttttctt aaatacactt ggagcaacg gtgcgttagg   24000 tcaagctccg tacatccacc tgattaaccg agatgagcac gaacagtatt acgctgtgtt   24060
cactggtagc ggaatccgag tgttcgacct ttctggtaac gagaagcaag ttaggtatcc   24120
taacggttcc aactacatca agaccgctaa tccacgtaac gacctgcgaa tggttactgt   24180
```

```
agcagactat acgttcatcg ttaaccgtaa cgttgttgca cagaagaaca caaagtctgt   24240
caacttaccg aattacaacc ctaatcaaga cggattgatt aacgttcgtg gtggtcagta   24300
tggtagggaa ctaattgtac acattaacgg taaagacgtt gcgaagtata agataccaga   24360
tggtagtcaa cctgaacacg taaacaatac ggatgcccaa tggttagctg aagagttagc   24420
caagcagatg cgcactaact tgtctgattg gactgtaaat gtagggcaag ggttcatcca   24480
tgtgaccgca cctagtggtc aacagattga ctccttcacg actaaagatg ctacgcaga   24540
ccagttgatt aaccctgtga cccactacgc tcagtcgttc tctaagctgc cacctaatgc   24600
tcctaacggc tacatggtga aaatcgtagg ggacgcctct aagtctgccg accagtatta   24660
cgttcggtat gacgctgagc ggaaagtttg gactgagact ttaggttgga cactgagga   24720
ccaagttcta tgggaaacca tgccacacgc tcttgtgcga gccgctgacg gtaatttcga   24780
cttcaagtgg cttgagtggt ctcctaagtc ttgtggtgac gttgacacca acccttggcc   24840
ttcttttgtt ggttcaagta ttaacgatgt gttcttcttc cgtaaccgct taggattcct   24900
tagtggggag aacatcatat tgagtcgtac agccaaatac ttcaacttct accctgcgtc   24960
cattgcgaac cttagtgatg acgaccctat agacgtagct gtgagtacca accgaatagc   25020
aatccttaag tacgccgttc cgttctcaga agagttactc atctggtccg atgaagcaca   25080
attcgtcctg actgcctcgg gtactctcac atctaagtcg gttgagttga acctaacgac   25140
ccagtttgac gtacaggacc gagcgagacc ttttgggatt gggcgtaatg tctactttgc   25200
tagtccgagg tccagcttca cgtccatcca caggtactac gctgtgcagg atgtcagttc   25260
cgttaagaat gctgaggaca ttacatcaca cgttcctaac tacatcccta atggtgtgtt   25320
cagtatttgc ggaagtggta cggaaaactt ctgttcggta ctatctcacg gggaccctag   25380
taaaatcttc atgtacaaat tcctgtacct gaacgaagag ttaaggcaac agtcgtggtc   25440
tcattgggac tttggggaaa acgtacaggt tctagcttgt cagagtatca gctcagatat   25500
gtatgtgatt cttcgcaatg agttcaatac gttcctagct agaatctctt tcactaagaa   25560
cgccattgac ttacagggag aaccctatcg tgcctttatg gacatgaaga ttcgatacac   25620
gattcctagt ggaacataca acgatgacac attcactacc tctattcata ttccaacaat   25680
ttatggtgca aacttcggga ggggcaaaat cactgtattg gagcctgatg gtaagataac   25740
cgtgtttgag caacctacgg ctgggtggaa tagcgaccct tggctgagac tcagcggtaa   25800
cttggaggga cgcatggtgt acattgggtt caacattaac ttcgtatatg agttctctaa   25860
gttcctcatc aagcagactg ccgacgacg gtctacctcc acggaagaca ttgggcgctt   25920
acagttacgc cgagcgtggg ttaactacga gaactctggt acgtttgaca tttatgttga   25980
gaaccaatcg tctaactgga agtacacaat ggctggtgcc cgattaggct ctaacactct   26040
gagggctggg agactgaact tagggaccgg acaatatcga ttccctgtgg ttggtaacgc   26100
caagttcaac actgtataca tcttgtcaga tgagactacc cctctgaaca tcattgggtg   26160
tggctgggaa ggtaactact acggagaag ttccggtatt taattaaata ttctccctgt   26220
ggtggctcga aattaatacg actcactata gggagaacaa tacgactacg ggagggtttt   26280
cttatgatga ctataagacc tactaaaagt acagactttg aggtattcac tccggctcac   26340
catgacattc ttgaagctaa ggctgctggt attgagccga gtttccctga tgcttccgag   26400
tgtgtcacgt tgagcctcta tgggttccct ctagctatcg gtggtaactg cggggaccag   26460
tgctggttcg ttacgagcga ccaagtgtgg cgacttagtg gaaaggctaa gcgaaagttc   26520
cgtaagttaa tcatggagta tcgcgataag atgcttgaga agtatgatac tctttggaat   26580
```

```
tacgtatggg taggcaatac gtcccacatt cgtttcctca agactatcgg tgcggtattc  26640
catgaagagt acacacgaga tggtcaattt cagttattta caatcacgaa aggaggataa  26700
ccatatgtgt tgggcagccg caatacctat cgctatatct ggcgctcagg ctatcagtgg  26760
tcagaacgct caggccaaaa tgattgccgc tcagaccgct gctggtcgtc gtcaagctat  26820
ggaaatcatg aggcagacga acatccagaa tgctgaccta tcgttgcaag ctcgaagtaa  26880
acttgaggaa gcgtccgccg agttgacctc acagaacatg cagaaggtcc aagctattgg  26940
gtctatccga gcggctatcg gagagagtat gcttgaaggt tcctcaatgg accgcattaa  27000
gcgagtcaca gaaggacagt tcattcggga agccaatatg gtaactgaga actatcgccg  27060
tgactaccaa gcaatcttcg cacagcaact tggtggtact caaagtgctg caagtcagat  27120
tgacgaaatc tataagagcg aacagaaaca gaagagtaag ctacgatgg ttctggaccc  27180 actggctatc atggggtctt ccgctgcgag tgcttacgca tccggtgcgt tcgactctaa  27240
gtccacaact aaggcaccta ttgttgccgc taaaggaacc aagacgggga ggtaatgagc  27300
tatgagtaaa attgaatctg cccttcaagc ggcacaaccg ggactctctc ggttacgtgg  27360
tggtgctgga ggtatgggct atcgtgcagc aaccactcag gccgaacagc caaggtcaag  27420
cctattggac accattggtc ggttcgctaa ggctggtgcc gatatgtata ccgctaagga  27480
acaacgagca cgagacctag ctgatgaacg ctctaacgag attatccgta agctgacccc  27540
tgagcaacgt cgagaagctc tcaacaacgg gaccottctg tatcaggatg acccatacgc  27600
tatggaagca ctccgagtca agactggtcg taacgctgcg tatcttgtgg acgatgacgt  27660
tatgcagaag ataaaagagg gtgtcttccg tactcgcgaa gagatggaag agtatcgcca  27720
tagtcgcctt caagagggcg ctaaggtata cgctgagcag ttcggcatcg accctgagga  27780
cgttgattat cagcgtggtt tcaacgggga cattaccgag cgtaacatct cgctgtatgg  27840
tgcgcatgat aacttcttga gccagcaagc tcagaagggc gctatcatga acagccgagt  27900
ggaactcaac ggtgtccttc aagaccctga tatgctgcgt cgtccagact ctgctgactt  27960
ctttgagaag tatatcgaca acggtctggt tactggcgca atcccatctg atgctcaagc  28020
cacacagctt ataagccaag cgttcagtga cgcttctagc cgtgctggtg gtgctgactt  28080
cctgatgcga gtcggtgaca agaaggtaac acttaacgga gccactacga cttaccgaga  28140
gttgattggt gaggaacagt ggaacgctct catggtcaca gcacaacgtt ctcagtttga  28200
gactgacgcg aagctgaacg agcagtatcg cttgaagatt aactctgcgc tgaaccaaga  28260
ggacccaagg acagcttggg agatgcttca aggtatcaag gctgaactag ataaggtcca  28320
acctgatgag cagatgacac cacaacgtga gtggctaatc tccgcacagg aacaagttca  28380
gaatcagatg aacgcatgga cgaaagctca ggccaaggct ctggacgatt ccatgaagtc  28440
aatgaacaaa cttgacgtaa tcgacaagca attccagaag cgaatcaacg gtgagtgggt  28500
ctcaacggat tttaaggata tgccagtcaa cgagaacact ggtgagttca agcatagcga  28560
tatggttaac tacgccaata agaagctcgc tgagattgac agtatggaca ttccagacgg  28620
tgccaaggat gctatgaagt tgaagtacct tcaagcggac tctaaggacg gagcattccg  28680
tacagccatc ggaaccatgg tcactgacgc tggtcaagag tggtctgccg ctgtgattaa  28740
cggtaagtta ccagaacgaa ccccagctat ggatgctctg cgcagaatcc gcaatgctga  28800
ccctcagttg attgctgcgc tatacccaga ccaagctgag ctattcctga cgatggacat  28860
gatggacaag cagggtattg accctcaggt tattcttgat gccgaccgac tgactgttaa  28920
gcggtccaaa gagcaacgct ttgaggatga taaagcattc gagtctgcac tgaatgcatc  28980
```

```
taaggctcct gagattgccc gtatgccagc gtcactgcgc gaatctgcac gtaagattta   29040
tgactccgtt aagtatcgct cggggaacga aagcatggct atggagcaga tgaccaagtt   29100
ccttaaggaa tctacctaca cgttcactgg tgatgatgtt gacggtgata ccgttggtgt   29160
gattcctaag aatatgatgc aggttaactc tgacccgaaa tcatgggagc aaggtcggga   29220
tattctggag gaagcacgta agggaatcat tgcgagcaac ccttggataa ccaataagca   29280
actgaccatg tattctcaag gtgactccat ttaccttatg gacaccacag gtcaagtcag   29340
agtccgatac gacaaagagt tactctcgaa ggtctggagt gagaaccaga agaaactcga   29400
agagaaagct cgtgagaagg ctctggctga tgtgaacaag cgagcaccta tagttgccgc   29460
tacgaaggcc cgtgaagctg ctgctaaacg agtccgagag aaacgtaaac agactcctaa   29520
gttcatctac ggacgtaagg agtaactaaa ggctacataa ggaggcccta atggataag    29580 tacgataaga acgtaccaag tgattatgat ggtctgttcc aaaaggctgc tgatgccaac   29640
ggggtctctt atgaccttt acgtaaagtc gcttggacag aatcacgatt tgtgcctaca   29700
gcaaaatcta agactggacc attaggcatg atgcaattta ccaaggcaac cgctaaggcc   29760
ctcggtctgc gagttaccga tggtccagac gacgaccgac tgaaccctga gttagctatt   29820
aatgctgccg ctaagcaact tgcaggtctg gtagggaagt ttgatggcga tgaactcaaa   29880
gctgcccttg cgtacaacca aggcgaggga cgcttgggta atccacaact tgaggcgtac   29940
tctaagggag acttcgcatc aatctctgag gagggacgta actacatgcg taaccttctg   30000
gatgttgcta agtcacctat ggctggacag ttggaaactt ttggtggcat aaccccaaag   30060
ggtaaaggca ttccggctga ggtaggattg gctggaattg gtcacaagca gaaagtaaca   30120
caggaacttc ctgagtccac aagttttgac gttaagggta tcgaacagga ggctacggcg   30180
aaaccattcg ccaaggactt ttgggagacc cacgagaaa cacttgacga gtacaacagt   30240
cgttcaacct tcttcggatt caaaaatgct gccgaagctg aactctccaa ctcagtcgct   30300
gggatggctt tccgtgctgg tcgtctcgat aatggttttg atgtgtttaa agacaccatt   30360
acgccgactc gctggaactc tcacatctga actccagagg agttagagaa gattcgaaca   30420
gaggttaaga accctgcgta catcaacgtt gtaactggtg gttcccctga gaacctcgat   30480
gacctcatta aattggctaa cgagaacttt gagaatgact cccgcgctgc cgaggctggc   30540
ctaggtgcca aactgagtgc tggtattatt ggtgctggtg tggacccgct tagctatgtt   30600
cctatggtcg gtgtcactgg taagggcttt aagttaatca ataaggctct tgtagttggt   30660
gccgaaagtg ctgctctgaa cgttgcatcc gaaggtctcc gtacctccgt agctggtggt   30720
gacgcagact atgcgggtgc tgccttaggt ggctttgtgt ttggcgcagg catgtctgca   30780
atcagtgacg ctgtagctgc tggactgaaa cgcagtaaac cagaagctga gttcgacaat   30840
gagttcatcg gtcctatgat gcgattggaa gcccgtgaga cagcacgaaa cgccaactct   30900
gcggacctct ctcggatgaa cactgagaac atgaagtttg aaggtgaaca taatggtgtc   30960
ccttatgagg acttaccaac agagagaggt gccgtggtgt acatgatgg ctccgttcta   31020 agtgcaagca acccaatcaa ccctaagact ctaaaagagt tctccgaggt tgaccctgag   31080
aaggctgcgc gaggaatcaa actggctggg ttcaccgaga ttggcttgaa gacctggggg   31140
tctgacgatg ctgacatccg tagagtggct atcgacctcg ttcgctctcc tactggtatg   31200
cagtctggtg cctcaggtaa gttcggtgca acagcttctg acatccatga gagacttcat   31260
ggtactgacc agcgtactta taatgacttg tacaaagcaa tgtctgacgc tatgaaagac   31320
cctgagttct ctactggcgg cgctaagatg tcccgtgaag aaactcgata cactatctac   31380
```

```
cgtagagcgg cactagctat tgagcgtcca gaactacaga aggcactcac tccgtctgag   31440
agaatcgtta tggacatcat taagcgtcac tttgacacca agcgtgaact tatggaaaac   31500
ccagcaatat tcggtaacac aaaggctgtg agtatcttcc ctgagagtcg ccacaaaggt   31560
acttacgttc ctcacgtata tgaccgtcat gccaaggcgc tgatgattca acgctacggt   31620
gccgaaggtt tgcaggaagg gattgcccgc tcatggatga acagctacgt ctccagacct   31680
gaggtcaagg ccagagtcga tgagatgctt aaggaattac acggggtgaa ggaagtaaca   31740
ccagagatgg tagagaagta cgctatggat aaggcttatg gtatctccca ctcagaccag   31800
ttcaccaaca gttccataat agaagagaac attgagggct tagtaggtat cgagaataac   31860
tcattccttg aggcacgtaa cttgtttgat tcggacctat ccatcactat gccagacgga   31920
cagcaattct cagtgaatga cctaaggggac ttcgatatgt tccgcatcat gccagcgtat   31980
gaccgccgtg tcaatggtga catcgccatc atggggtcta ctggtaaaac cactaaggaa   32040
cttaaggatg agattttggc tctcaaagcg aaagctgagg gagacggtaa gaagactggc   32100
gaggtacatg ctttaatgga taccgttaag attcttactg gtcgtgctag acgcaatcag   32160
gacactgtgt gggaaacctc actgcgtgcc atcaatgacc tagggttctt cgctaagaac   32220
gcctacatgg gtgctcagaa cattacggag attgctggga tgattgtcac tggtaacgtt   32280
cgtgctctag ggcatggtat cccaattctg cgtgatacac tctacaagtc taaaccagtt   32340
tcagctaagg aactcaagga actccatgcg tctctgttcg ggaaggaggt ggaccagttg   32400
attcggccta acgtgctga cattgtgcag cgcctaaggg aagcaactga taccggacct   32460
gccgtggcga acatcgtagg gaccttgaag tattcaacac aggaactggc tgctcgctct   32520
ccgtggacta agctactgaa cggaaccact aactacctt c tggatgctgc gcgtcaaggt   32580
atgcttgggg atgttattag tgccaccta acaggtaaga ctacccgctg ggagaaagaa   32640
ggcttccttc gtggtgcctc cgtaactcct gagcagatgg ctggcatcaa gtctctcatc   32700
aaggaacata tggtacgcgg tgaggacggg aagtttaccg ttaaggacaa gcaagcgttc   32760
tctatggacc cacgggctat ggacttatgt agactggctg acaaggtagc tgatgaggca   32820
atgctgcgtc cacataaggt gtccttacag gattcccatg cgttcggagc actaggtaag   32880
atggttatgc agtttaagtc tttcactatc aagtccctta actctaagtt cctgcgaacc   32940
ttctatgatg gatacaagaa caaccgagcg attgacgctg cgctgagcat catcacctct   33000
atgggtctcg ctggtggttt ctatgctatg gctgcacacg tcaaagcata cgctctgcct   33060
aaggagaaac gtaaggagta cttggagcgt gcactggacc caaccatgat tgcccacgct   33120
gcgttatctc gtagttctca attgggtgct cctttggcta tggttgacct agttggtggt   33180
gttttagggt tcgagtcctc caagatggct cgctctacga ttctacctaa ggacaccgtg   33240
aaggaacgtg acccaaacaa accgtacacc tctagagagg taatgggcgc tatgggttca   33300
aaccttctgg aacagatgcc ttcggctggc tttgtggcta acgtagggc taccttaatg   33360 aatgctgctg gcgtggtcaa ctcacctaat aaagcaaccg agcaggactt catgactggt   33420
cttatgaact ccacaaaaga gttagtaccg aacgacccat tgactcaaca gcttgtgttg   33480
aagatttatg aggcgaacgg tgttaacttg agggagcgta ggaaataata cgactcacta   33540
tagggagagg cgaaataatc ttctccctgt agtctcttag atttacttta aggaggtcaa   33600
atggctaacg taattaaaac cgttttgact taccagttag atggctccaa tcgtgatttt   33660
aatatcccgt ttgagtatct agcccgtaag ttcgtagtgg taactcttat tggtgtagac   33720
cgaaaggtcc ttacgattaa tacagactat cgctttgcta cacgtactac tatctctctg   33780
```

```
acaaaggctt ggggtccagc cgatggctac acgaccatcg agttacgtcg agtaacctcc   33840
actaccgacc gattggttga ctttacggat ggttcaatcc tccgcgcgta tgaccttaac   33900
gtcgctcaga ttcaaacgat gcacgtagcg gaagaggccc gtgacctcac tacggatact   33960
atcggtgtca ataacgatgg tcacttggat gctcgtggtc gtcgaattgt gaacctagcg   34020
aacgccgtgg atgaccgcga tgctgttccg tttggtcaac taaagaccat gaaccagaac   34080
tcatggcaag cacgtaatga agccttacag ttccgtaatg aggctgagac tttcagaaac   34140
caagcggagg gctttaagaa cgagtccagt accaacgcta cgaacacaaa gcagtggcgc   34200
gatgagacca agggtttccg agacgaagcc aagcggttca agaatacggc tggtcaatac   34260
gctacatctg ctgggaactc tgcttccgct gcgcatcaat ctgaggtaaa cgctgagaac   34320
tctgccacag catccgctaa ctctgctcat ttggcagaac agcaagcaga ccgtgcggaa   34380
cgtgaggcag acaagctgga aaattacaat ggattggctg gtgcaattga taggtagat   34440 ggaaccaatg tgtactggaa aggaaatatt cacgctaacg ggcgccttta catgaccaca   34500
aacggttttg actgtggcca gtatcaacag ttctttggtg gtgtcactaa tcgttactct   34560
gtcatggagt ggggagatga gaacggatgg ctgatgtatg ttcaacgtag agagtggaca   34620
acagcgatag gcggtaacat ccagttagta gtaaacggac agatcatcac ccaaggtgga   34680
gccatgaccg gtcagctaaa attgcagaat gggcatgttc ttcaattaga gtccgcatcc   34740
gacaaggcgc actatattct atctaaagat ggtaacagga ataactggta cattggtaga   34800
gggtcagata caacaatga ctgtaccttc cactcctatg tacatggtac gaccttaaca   34860
ctcaagcagg actatgcagt agttaacaaa cacttccacg taggtcaggc cgttgtggcc   34920
actgatggta atattcaagg tactaagtgg ggaggtaaat ggctggatgc ttacctacgt   34980
gacagcttcg ttgcgaagtc caaggcgtgg actcaggtgt ggtctggtag tgctggcggt   35040
ggggtaagtg tgactgtttc acaggatctc cgcttccgca atatctggat taagtgtgcc   35100
aacaactctt ggaacttctt ccgtactggc cccgatggaa tctacttcat agcctctgat   35160
ggtggatggt tacgattcca aatacactcc aacggtctcg gattcaagaa tattgcagac   35220
agtcgttcag tacctaatgc aatcatggtg gagaacgagt aattggtaaa tcacaaggaa   35280
agacgtgtag tccacggatg gactctcaag gaggtacaag gtgctatcat tagactttaa   35340
caacgaattg attaaggctg ctccaattgt tgggacgggt gtagcagatg ttagtgctcg   35400
actgttcttt gggttaagcc ttaacgaatg gttctacgtt gctgctatcg cctacacagt   35460
ggttcagatt ggtgccaagg tagtcgataa gatgattgac tggaagaaag ccaataagga   35520
gtgatatgta tggaaaagga taagagcctt attacattct tagagatgtt ggacactgcg   35580
atggctcagc gtatgcttgc ggacctttcg gaccatgagc gtcgctctcc gcaactctat   35640
aatgctatta acaaactgtt agaccgccac aagttccaga ttggtaagtt gcagccggat   35700
gttcacatct taggtggcct tgctggtgct cttgaagagt acaaagagaa agtcggtgat   35760
aacggtctta cggatgatga tatttacaca ttacagtgat atactcaagg ccactacaga   35820
tagtggtctt tatggatgtc attgtctata cgagatgctc ctacgtgaaa tctgaaagtt   35880
aacgggaggc attatgctag aattttacg taagctaatc ccttgggttc tcgctgggat   35940
gctattcggg ttaggatggc atctagggtc agactcaatg gacgctaaat ggaaacagga   36000
ggtacacaat gagtacgtta agagagttga ggctgcgaag agcactcaaa gagcaatcga   36060
tgcggtatct gctaagtatc aagaagacct tgccgcgctg gaagggagca ctgataggat   36120
tatttctgat ttgcgtagcg acaataagcg gttgcgcgtc agagtcaaaa ctaccggaac   36180
```

```
ctccgatggt cagtgtggat tcgagcctga tggtcgagcc gaacttgacg accgagatgc   36240
taaacgtatt ctcgcagtga cccagaaggg tgacgcatgg attcgtgcgt tacaggatac   36300
tattcgtgaa ctgcaacgta agtaggaaat caagtaagga ggcaatgtgt ctactcaatc   36360
caatcgtaat gcgctcgtag tggcgcaact gaaaggagac ttcgtggcgt tcctattcgt   36420
cttatggaag gcgctaaacc taccggtgcc cactaagtgt cagattgaca tggctaaggt   36480
gctggcgaat ggagacaaca agaagttcat cttacaggct ttccgtggta tcggtaagtc   36540
gttcatcaca tgtgcgttcg ttgtgtggtc cttatggaga gaccctcagt tgaagatact   36600
tatcgtatca gcctctaagg agcgtgcaga cgctaactcc atctttatta agaacatcat   36660
tgacctgctg ccattcctat ctgagttaaa gccaagaccc ggacagcgtg actcggtaat   36720
cagctttgat gtaggcccag ccaatcctga ccactctcct agtgtgaaat cagtaggtat   36780
cactggtcag ttaactggta gccgtgctga cattatcatt gcggatgacg ttgagattcc   36840
gtctaacagc gcaactatgg gtgcccgtga gaagctatgg actctggttc aggagttcgc   36900
tgcgttactt aaaccgctgc cttcctctcg cgttatctac cttggtacac ctcagacaga   36960
gatgactctc tataaggaac ttgaggataa ccgtgggtac acaaccatta tctgcctgc    37020 tctgtaccca aggacacgtg aagagaacct ctattactca cagcgtcttg ctcctatgtt   37080
acgcgctgag tacgatgaga accctgaggc acttgctggg actccaacag acccagtgcg   37140
ctttgaccgt gatgacctgc gcgagcgtga gttggaatac ggtaaggctg ctttacgct    37200 acagttcatg cttaacccta accttagtga tgccgagaag tacccgctga ggcttcgtga   37260
cgctatcgta gcggccttag acttagagaa ggccccaatg cattaccagt ggcttccgaa   37320
ccgtcagaac atcattgagg accttcctaa cgttggcctt aagggtgatg acctgcatac   37380
gtaccacgat tgttccaaca actcaggtca gtaccaacag aagattctgg tcattgaccc   37440
tagtggtcgc ggtaaggacg aaacaggtta cgctgtgctg tacacactga acggttacat   37500
ctaccttatg gaagctggag gtttccgtga tggctactcc gataagaccc ttgagttact   37560
cgctaagaag gcaaagcaat ggggagtcca gacggttgtc tacgagagta acttcggtga   37620
cggtatgttc ggtaaggtat tcagtcctat ccttcttaaa caccacaact gtgcgatgga   37680
agagattcgt gcccgtggta tgaaagagat gcgtatttgc gatacccttg agccagtcat   37740
gcagactcac cgccttgtaa ttcgtgatga ggtcattagg gccgactacc agtccgctcg   37800
tgacgtagac ggtaagcatg acgttaagta ctcgttgttc taccagatga cccgtatcac   37860
tcgtgagaaa ggcgctctgg ctcatgatga ccgattggat gcccttgcgt taggcattga   37920
gtatctccgt gagtccatgc agttggattc cgttaaggtc gagggtgaag tacttgctga   37980
cttccttgag gaacacatga tgcgtcctac ggttgctgct acgcatatca ttgagatgtc   38040
tgtgggagga gttgatgtgt actctgagga cgatgagggt tacggtacgt ctttcattga   38100
gtggtgattt atgcattagg actgcatagg gatgcactat agaccacgga tggtcagttc   38160
tttaagttac tgaaaagaca cgataaatta atacgactca ctatagggag aggagggacg   38220
aaaggttact atatagatac tgaatgaata cttatagagt gcataaagta tgcataatgg   38280
tgtacctaga gtgacctcta agaatggtga ttatattgta ttagtatcac cttaacttaa   38340
ggaccaacat aaagggagga gactcatgtt ccgcttattg ttgaacctac tgcggcatag   38400
agtcacctac cgatttcttg tggtactttg tgctgcccct gggtacgcat ctcttactgg   38460
agacctcagt tcactggagt ctgtcgtttg ctctatactc acttgtagcg attagggtct   38520
tcctgaccga ctgatggctc accgagggat tcagcggtat gattgcatca caccacttca   38580
```

-continued

```
tccctataga gtcaagtcct aaggtatacc cataaagagc ctctaatggt ctatcctaag  38640
gtctatacct aaagataggc catcctatca gtgtcaccta aagagggtct tagagagggc  38700
ctatggagtt cctatagggt cctttaaaat ataccataaa aatctgagtg actatctcac  38760
agtgtacgga cctaaagttc ccccataggg ggtacctaaa gcccagccaa tcacctaaag  38820
tcaaccttcg gttgaccttg agggttccct aagggttggg gatgaccctt gggtttgtct  38880
ttgggtgtta ccttgagtgt ctctctgtgt ccct                              38914

<210> SEQ ID NO 10
<211> LENGTH: 403
<212> TYPE: DNA
<213> ORGANISM: Homo sapiens

<400> SEQUENCE: 10
ttttgcaccg gatgtaattt aatagggtgg ggaagatact caagagcggg catgggacgg     60
ggcgcagagt ccgggttaag ggccttacgt agccaaaagg ggggatccag gaccctcggg    120 ccccccccagc cgcatctgca ggttgatgcg gtacgctgaa gactacagag tgcctggcct   180
ttgcgggaca agcgtagacc gcgaatgggg acagccgggg acagagcagc gcgcggcggg    240
cctgaggggg atggccgctg agacactgcc gtgggggcgg ggaccagggt gggaaggaaa    300
gggtggaacc tgtgctccgc tgcagtagcg caccatgggg gccggagcgc agcccgccct    360
ccccgccgct cgccccgtgc gccccccccg gcctccccgc cca                      403
```